(12) United States Patent
Meunier et al.

(10) Patent No.: US 7,649,091 B2
(45) Date of Patent: Jan. 19, 2010

(54) ORALLY BIOAVAILABLE LOW MOLECULAR WEIGHT METALLOPORPHYRINS AS ANTIOXIDANTS

(75) Inventors: Bernard Meunier, Castanet (FR); Frederic Cosledan, Labege (FR)

(73) Assignee: Eukarion, Inc., Woburn, MA (US)

( * ) Notice: Subject to any disclaimer, the term of this patent is extended or adjusted under 35 U.S.C. 154(b) by 0 days.

(21) Appl. No.: 10/559,221

(22) PCT Filed: Jun. 3, 2004

(86) PCT No.: PCT/US2004/017560

§ 371 (c)(1),
(2), (4) Date: Jun. 19, 2006

(87) PCT Pub. No.: WO2005/000854

PCT Pub. Date: Jan. 6, 2005

(65) Prior Publication Data

US 2006/0241095 A1 Oct. 26, 2006

Related U.S. Application Data

(60) Provisional application No. 60/476,765, filed on Jun. 6, 2003.

(51) Int. Cl.
C07B 47/00 (2006.01)
C07D 487/22 (2006.01)

(52) U.S. Cl. .................................................. 540/145

(58) Field of Classification Search .................. None
See application file for complete search history.

(56) References Cited

U.S. PATENT DOCUMENTS 4,895,682 A * 1/1990 Ellis et al. .................. 554/135
5,571,908 A * 11/1996 Wijesekera et al. ......... 540/145
6,127,356 A 10/2000 Crapo et al.

FOREIGN PATENT DOCUMENTS

WO WO 97/20846 6/1997
WO WO 02/04454 1/2002
WO WO 02/096366 12/2002

OTHER PUBLICATIONS

Sato, et. al., International Journal of Nanoscience (2002), 1(5 & 6), 489-494.*
Jinshi et al. "Diaryl porphine photosensitizer, its preparation and application", XP002304532, 2004, Database Caplus—Chemical Abstracts Services.
Senge and Feng, "Regioselective reaction of 5, 15-disubstituted porphyrins with organolithium reagents-synthetic access to 5, 10, 15-trisubstituted porphyrins and directly meso-meso-linked bisporphyrins", J. Chem. Soc., Perkin Trans, 2000, 3615-3621.
Song et al., "Metal dependence of the contributions of low-frequency normal coordinates to the sterically induced distortions of meso-dialkyl-substituted porphyrins", Inorg. Chem, 1998, 37, 2009-2019.
Wiehe, et al., "A practical synthesis of meso-monosubstituted, β-unsubstituted porphyrins", Organic letters, 2002, vol. 4, No. 22, 3807-3809.
Wiehe, et al., "Hydrophilicity vs hydrophobicity-varying the amphiphilic structure of porphyrins related to the photosensitizer m-THPC", Journal of porphyrins and Phthalocyanines, 2001, vol. 5, No. 10, pp. 758-761.
Wertsching, et al. "On the negligible impact of ruffling on the electronic spectra of porphine, tetramethylporphyrin, and perfluoroalkylporphyrins", Journal of the American Chemistry Society, 2001, 123(17), 3932-3939.

* cited by examiner

Primary Examiner—James O Wilson
Assistant Examiner—Jeffrey H Murray
(74) Attorney, Agent, or Firm—Carol L. Francis; Bozicevic, Field & Francis LLP

(57) ABSTRACT

The invention relates to compounds which are orally bioavailable water soluble metalloporphyrins. These compounds, e.g. represented by Structural Formula (I): wherein R1 and R2 are each independently lower alkyl, cycloalkyl, halogen substituted alkyl or substituted or unsubstituted phenyl groups, are synthetic catalytic scavengers of reactive oxygen chemical species. The invention also relates to pharmaceutical compositions comprising these compounds and to methods of use of these compounds for preventing or arresting free radical associated diseases or conditions.

7 Claims, 5 Drawing Sheets

Table 1. Crystal Data and Structure Refinement for Compound 17

| | |
|---|---|
| Identification code | fred4m |
| Empirical formula | C44 H42 N4 O6 |
| Formula weight | 722.82 |
| Temperature | 173(2) K |
| Wavelength | 0.71073 Å |
| Crystal system | Triclinic |
| Space group | P-1 |
| Unit cell dimensions | a = 9.081(18) Å, $\alpha$ = 118.91(4)°. |
| | b = 10.94(2) Å, $\beta$ = 104.16(4)°. |
| | c = 11.12(2) Å, $\gamma$ = 92.04(4)°. |
| Volume | 923(3) Å$^3$ |
| Z | 1 |
| Density (calculated) | 1.301 Mg/m$^3$ |
| Absorption coefficient | 0.087 mm$^{-1}$ |
| F(000) | 382 |
| Crystal size | 0.05 x 0.1 x 0.8 mm$^3$ |
| Theta range for data collection | 2.16 to 21.96°. |
| Index ranges | -9<=h<=9, -11<=k<=11, -8<=l<=11 |
| Reflections collected | 3453 |
| Independent reflections | 2184 [R(int) = 0.1577] |
| Completeness to theta = 21.96° | 97.0 % |
| Absorption correction | None |
| Refinement method | Full-matrix least-squares on F$^2$ |
| Data / restraints / parameters | 2184 / 0 / 248 |
| Goodness-of-fit on F$^2$ | 1.048 |
| Final R indices [I>2sigma(I)] | R1 = 0.0743, wR2 = 0.1721 |
| R indices (all data) | R1 = 0.1245, wR2 = 0.2048 |
| Largest diff. peak and hole | 0.267 and -0.263 e.Å$^{-3}$ |

FIG. 2

Table 2. Bond Length [Å] and Angles [°] for Compound 17

| | |
|---|---|
| N(1)-C(2) | 1.376(7) |
| N(1)-C(5) | 1.389(8) |
| N(2)-C(7) | 1.382(7) |
| N(2)-C(10) | 1.385(7) |
| C(1)-C(2) | 1.410(8) |
| C(1)-C(10)#1 | 1.414(8) |
| C(1)-C(11) | 1.519(8) |
| C(2)-C(3) | 1.435(8) |
| C(3)-C(4) | 1.360(8) |
| C(4)-C(5) | 1.424(8) |
| C(5)-C(6) | 1.383(8) |
| C(6)-C(7) | 1.385(8) |
| C(7)-C(8) | 1.448(8) |
| C(8)-C(9) | 1.338(8) |
| C(9)-C(10) | 1.452(8) |
| C(10)-C(1)#1 | 1.414(8) |
| C(11)-C(12) | 1.394(8) |
| C(11)-C(16) | 1.423(8) |
| C(12)-C(13) | 1.392(8) |
| C(13)-C(14) | 1.397(8) |
| C(14)-O(1) | 1.376(6) |
| C(14)-C(15) | 1.397(8) |
| C(15)-C(16) | 1.389(7) |
| O(1)-C(17) | 1.448(7) |
| C(17)-C(18) | 1.503(8) |
| C(18)-C(19) | 1.536(9) |
| C(19)-C(20) | 1.501(8) |
| C(20)-O(2) | 1.462(8) |
| O(2)-C(21) | 1.336(8) |
| C(21)-O(3) | 1.217(7) |
| C(21)-C(22) | 1.514(9) |
| | |
| C(2)-N(1)-C(5) | 110.2(4) |
| C(7)-N(2)-C(10) | 105.3(4) |

FIG. 3A

Table 2. - Cont.

| | |
|---|---|
| C(2)-C(1)-C(10)#1 | 124.3(5) |
| C(2)-C(1)-C(11) | 118.5(5) |
| C(10)#1-C(1)-C(11) | 117.3(5) |
| N(1)-C(2)-C(1) | 125.1(5) |
| N(1)-C(2)-C(3) | 106.5(5) |
| C(1)-C(2)-C(3) | 128.4(5) |
| C(4)-C(3)-C(2) | 108.2(5) |
| C(3)-C(4)-C(5) | 108.8(5) |
| C(6)-C(5)-N(1) | 125.7(5) |
| C(6)-C(5)-C(4) | 128.0(6) |
| N(1)-C(5)-C(4) | 106.3(5) |
| C(5)-C(6)-C(7) | 130.7(6) |
| N(2)-C(7)-C(6) | 125.5(5) |
| N(2)-C(7)-C(8) | 110.1(5) |
| C(6)-C(7)-C(8) | 124.4(5) |
| C(9)-C(8)-C(7) | 107.4(5) |
| C(8)-C(9)-C(10) | 107.2(5) |
| N(2)-C(10)-C(1)#1 | 124.2(5) |
| N(2)-C(10)-C(9) | 110.0(5) |
| C(1)#1-C(10)-C(9) | 125.8(5) |
| C(12)-C(11)-C(16) | 118.1(5) |
| C(12)-C(11)-C(1) | 121.7(5) |
| C(16)-C(11)-C(1) | 120.1(5) |
| C(13)-C(12)-C(11) | 121.9(5) |
| C(12)-C(13)-C(14) | 119.7(5) |
| O(1)-C(14)-C(13) | 124.1(5) |
| O(1)-C(14)-C(15) | 116.6(5) |
| C(13)-C(14)-C(15) | 119.2(5) |
| C(16)-C(15)-C(14) | 121.3(5) |
| C(15)-C(16)-C(11) | 119.7(5) |
| C(14)-O(1)-C(17) | 119.4(4) |
| O(1)-C(17)-C(18) | 108.4(5) |
| C(17)-C(18)-C(19) | 108.9(5) |
| C(20)-C(19)-C(18) | 113.9(5) |
| O(2)-C(20)-C(19) | 105.3(5) |
| C(21)-O(2)-C(20) | 116.7(5) |

FIG. 3B

Table 2. - Cont.

| | |
|---|---|
| O(3)-C(21)-O(2) | 122.4(6) |
| O(3)-C(21)-C(22) | 127.7(6) |
| O(2)-C(21)-C(22) | 109.9(5) |

Symmetry transformations used to generate equivalent atoms:
1 -x+1,-y+2,-z+2

FIG. 3C

ORALLY BIOAVAILABLE LOW MOLECULAR WEIGHT METALLOPORPHYRINS AS ANTIOXIDANTS

RELATED APPLICATION DATA

This application is a 371 of PCT/US2004/017560 filed Jun. 3, 2004 which claims priority from U.S. Provisional Application No. 60/476,765 filed Jun. 6, 2003.

RELATED APPLICATION

This application claims the benefit of U.S. Provisional Application No. 60/476,765, filed Jun. 6, 2003. The entire teachings of the above application are incorporated herein by reference.

BACKGROUND OF THE INVENTION

Molecular oxygen is an essential nutrient for nonfacultative aerobic organisms, including humans. Oxygen, although essential for aerobic metabolism, can be converted to poisonous metabolites, such as superoxide anion and hydrogen peroxide, collectively known as reactive oxygen species. Excessive concentrations of various forms of oxygen and of free radicals can have serious adverse effects on living systems, including the peroxidation of membrane lipids, the hydroxylation of nucleic acid bases, and the oxidation of sulfhydryl groups and other sensitive moieties in proteins. If uncontrolled, mutations and cell death result.

Biological antioxidants include well-defined naturally occurring metalloenzymes, such as superoxide dismutase (SOD), catalase (CAT), and selenium glutathione peroxidase, as well as the enzyme, phospholipid hydroperoxide glutathione peroxidase. A large number of diseases or degenerative processes are related to disorders with metalloenzymes involved in the detoxification of reactive oxygen species derived from dioxygen reduction. The role of these metalloenzymes has been demonstrated with animals under-expressing SOD or CAT enzymes. In addition, the induction of nitric oxide-dependent apoptosis in motor neurons by zinc-deficient superoxide dismutase has recently been shown (Estévez et al. (2000), Science, 286:2498-2500).

Reactive oxygen species are key executioners in Fas-induced hepatocyte apoptosis. (Malassagne et al., *Gastroenterology* 121:1451-1459 (2001)). Human Fas ligand is a polypeptide which has been reported by Nagata et al. to be a biological molecule which induces apoptosis of Fas-expressing cells (Takahashi, T. et al., *International Immunology*, vol, 6, 1567-1574, 1994). Human Fas ligand is a Type II membrane protein of TNF family with a molecular weight of about 40 kD. The extracellular domain of the human Fas ligand is highly homologous with the extracellular domain of rat Fas ligand (Suda, T. et al., *Cell*, vol. 75, 1169-1178, 1993) and mouse Fas ligand (Takahashi, T. et al., *Cell*, vol. 76, 969-976, 1994). The human Fas ligand recognizes not only the human Fas but also the mouse Fas to induce the apoptosis, and vice versa, the rat Fas ligand and the mouse Fas ligand also recognize the human Fas to induce the apoptosis.

Considerable research has been done on the mechanism of signal transduction in the cell upon the Fas-mediated apoptosis, and identification and cloning of the factor which interacts with the intracellular domain of the Fas, in particular, the region called "death domain" to transmit or block the signal have been reported. Possibility of the involvement of ICE (interleukin-1-converting enzyme)-related thiol proteases in the Fas-mediated apoptosis has also been indicated. Fas-Fas ligand interaction plays a major role in hepatoctye injury during viral hepatitis through the activation of caspases or through mitochondrial disruption.

Obstacles exist for the use of recombinant metalloenzymes in therapy including: solution instability, limited cellular accessibility, orally bioavailability, immunogenicity, short half-lives, cost of production and proteolytic digestion. These synthetic catalytic scavengers must be stable in physiological conditions and, in particular, the metal should be strictly inserted within the ligand to avoid any demetallation and trapping of the metal on by serum proteins. These synthetic catalytic scavengers must also be soluble in water at pH 7.0. It is desirable that the compositions are orally bioavailable. Avoiding synthetic molecules that lead to DNA cleavage is an additional concern.

Consequently, there is a need for new oral bioavailable synthetic transition metal complexes with the ability to scavenge reactive oxygen species derived from the non-controlled reduction of dioxygen. The need exists for providing low molecular weight, orally bioavailable water soluble metallophorphyrin derivatives able to scavenge reactive oxygen species.

SUMMARY OF THE INVENTION

The present invention relates to compounds that are orally bioavailable, low molecular weight and effective as synthetic catalytic scavengers for reactive oxygen species. The compounds are effective as superoxide dismutase (SOD), and/or catalase (CAT) and/or peroxidase (POD) mimetics that accordingly, have antioxidant and/or free radical scavenging properties and function in vivo as antioxidants. In particular, the present invention relates to oral bioavailable water soluble metalloenzyme mimetics, pharmaceutical formulations containing them, methods for their preparation and the use of such compounds in prophylaxis and therapy for diseases and degenerative processes resulting from reactive oxygen species. In certain embodiments, the compounds of the present invention can be non-genotoxic.

In one embodiment, the metallophorphyrin derivatives of this invention can be represented by Structural Formula I:

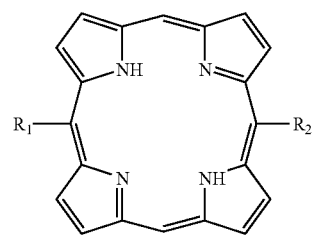

Structural Formula I wherein R1 and R2 are each independently aliphatic, lower alkyl, cycloalkyl, halogen substituted alkyl, phenyl or substituted phenyl groups.

In certain embodiments, Structural Formula I compound is a complex with a first row transition metal ion such as manganese, iron, cobalt, copper, nickel and zinc.

In other embodiments, R1 and R2 are cyclopropyl groups.

In one aspect, the invention provides pharmaceutical formulations comprising one or more pharmaceutically acceptable carriers, diluents or excipients and a therapeutically effective amount of compound represented by Structural Formula I.

In certain embodiment, the pharmaceutical formulation is represented by Structural Formula I is a complex with a first row transition metal ion, wherein R1 and R2 are both either cyclopropyl or phenyl groups.

In yet another embodiment, the invention relates to methods of administering a pharmaceutically effective porphyrin compound to an individual in need thereof, comprising orally introducing a compound of Structural Formula I into said individual wherein said compound becomes bioavailable by passing from the lumen of the alimentary canal to the bloodstream of said individual.

In certain embodiments, the compound reduces oxyradical- or reactive oxygen-induced damage to cells of said individual as a consequence of said compound becoming bioavailable. Also described are methods of treating, preventing or arresting a free radical associated disease or condition comprising administering to a mammal in need of a therapeutically effective amount of Structural Formula I. In yet another embodiment, the invention relates to a method of reducing oxyradical- or reactive oxygen-induced damage to cells comprising introducing a compound of Structural Formula I to said cells wherein said introducing results in a decrease in the amount of free oxygen radical or nonradical reactive oxygen species in said cells when compared to not introducing said compound, wherein said decrease in the amount of free oxygen radical or nonradical reactive oxygen species reduces oxyradical- or reactive oxygen-induced damage to said cells. In certain embodiments, the oxyradical or reactive oxygen-induced damage is damage resulting from a stroke, Alzheimer's disease, dementia, Parkinson's disease, Lou Gehrig disease, motor neuron disorders, Huntington's disease, cancer, multiple sclerosis, systemic lupus erythematosus, scleroderma, eczema, dermatitis, delayed type hypersensitivity, psoriasis, gingivitis, adult respiratory distress syndrome, septic shock, multiple organ failure, inflammatory diseases, asthma, allergic rhinitis, pneumonia, emphysema, chronic bronchitis, AIDS, inflammatory bowel disease, gastric ulcers, pancreatitis, transplantation rejection, atherosclerosis, hypertension, congestive heart failure, myocardial ischemic disorders, angioplasty, endocarditis, retinopathy of prematurity, cataract formation, uveitis, rheumatoid arthritis, oxygen toxicity, herpes simplex infection, burns, osteoarthritis, aging, diseases associated with abnormal apoptosis and diseases associated with abnormal levels of Fas antigen.

In other embodiments, the invention relates to methods of treating, preventing or arresting a free radical associated disease or condition comprising administering to a mammal in need of a therapeutically effective amount of a compound of Structural Formula I, comprising orally introducing the compound into said individual wherein said compound becomes bioavailable by passing from the lumen of the alimentary canal to the bloodstream of said individual wherein said compound reduces oxyradical- or reactive oxygen-induced damage to cells of said individual as a consequence of said compound becoming bioavailable wherein said introducing results in a decrease in the amount of free oxygen radical or nonradical reactive oxygen species in said cells when compared to not introducing said compound, wherein said decrease in the amount of free oxygen radical or nonradical reactive oxygen species reduces oxyradical- or reactive oxygen-induced damage to said cells.

In other embodiments, the invention relates to compounds represented by Structural Formula II:

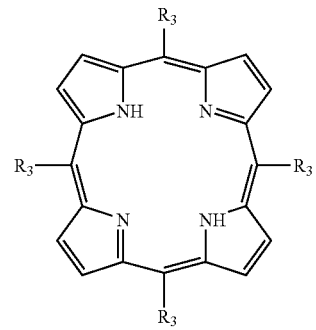

Structural Formula II wherein R3 is an aliphatic, lower allyl, cycloalkyl, and halogen substituted alkyl groups.

In certain embodiments, the compound is a complex with a first row transition metal ion such as manganese, iron, cobalt, copper, nickel and zinc.

In certain embodiments, R3 is cyclopropyl. The invention also relates to pharmaceutical formulations comprising one or more pharmaceutically acceptable carriers, diluents or excipients and a therapeutically effective amount of a compound of Structural formula II. In certain aspects, the pharmaceutical formulation comprises Structural Formula II wherein R3 is cyclopropyl. The invention also relates to methods of administering a pharmaceutically effective porphyrin compound to an individual in need thereof, comprising orally introducing a compound of Structural Formula II into said individual wherein said compound becomes bioavailable by passing from the lumen of the alimentary canal to the bloodstream of said individual. In certain embodiments, compound reduces oxyradical- or reactive oxygen-induced damage to cells of said individual as a consequence of said compound becoming bioavailable.

The invention further relates to compounds represented by Structural Formula III:

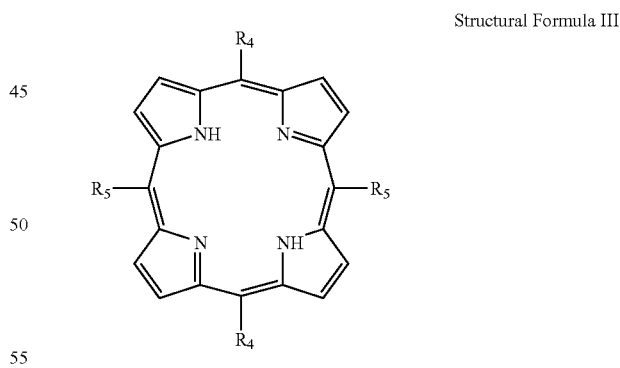

Structural Formula III wherein R4 is an aliphatic, lower alkyl, halogen substituted alkyl, cycloalkyl, substituted phenyl group or phenyl group and R5 is lower alkyl, halogen substituted alkyl or cycloalkyl group, further wherein R4 and R5 are not the same. In certain aspects, the compound of Structural Formula III is a complex with a first row transition metal ion such as manganese, iron, cobalt, copper, nickel and zinc.

In certain aspects, the invention relates to compounds of Structural Formula III wherein R4 is cyclopropyl and R5 is a lower alkyl, halogen substituted alkyl or cycloalkyl group. In other embodiments, the compounds are in a complex with a transition metal ion selected from the group consisting of manganese, iron, cobalt, copper, nickel and zinc.

The invention also relates to pharmaceutical formulations comprising one or more pharmaceutically acceptable carriers, diluents or excipients and a therapeutically effective amount of at least one compound of Structural Formula III.

In other embodiments, the pharmaceutical composition comprises Structural Formula III wherein R4 is cyclopropyl and R5 is a lower alkyl, halogen substituted alkyl or cycloalkyl group. The invention also relates to methods of administering a pharmaceutically effective porphyrin compound to an individual in need thereof, comprising orally introducing a compound Structural Formula III into an individual wherein the compound becomes bioavailable by passing from the lumen of the alimentary canal to the bloodstream of the individual. In other embodiments, the compound reduces oxyradical- or reactive oxygen-induced damage to cells of the individual as a consequence of said compound becoming bioavailable.

The invention further relates to compounds represented by Structural Formula IV:

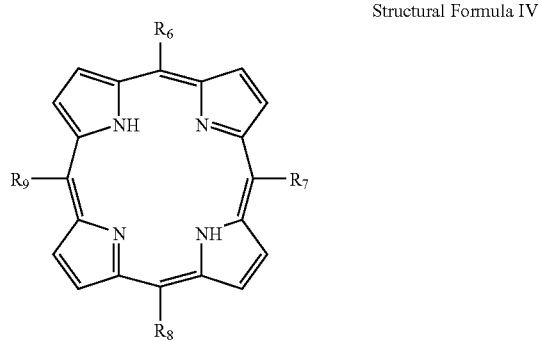

Structural Formula IV wherein R6, R7 and R8 are each independently hydrogen, an aliphatic group, lower alkyl, halogen substituted alkyl, cycloalkyl, substituted phenyl groups or unsubstituted phenyl groups and R9 is a lower alkyl, halogen substituted alkyl, cycloalkyl, substituted phenyl group or unsubstituted phenyl group wherein the groups at positions R6, R7, R8 and R9 are not all the same and R6 and R8 cannot be the same when R7 and R9 are the same. In certain embodiments, the compound is a complex with a first row transition metal ion, such as manganese, iron, cobalt, copper, nickel and zinc.

In other embodiments, R6, R7 and R8 of Structural Formula IV are hydrogen or lower alkyl groups and R9 is cyclopropyl. In certain aspects, the compound is a complex with a transition metal ion such as manganese, iron, cobalt, copper, nickel and zinc.

In other embodiments, R6, is hydrogen and R7, R8 and R9 of Structural Formula IV are cyclopropyl groups. In certain aspects of the invention, the compound is a complex with a transition metal ion such as manganese, iron, cobalt, copper, nickel and zinc.

BRIEF DESCRIPTION OF THE DRAWINGS

FIG. 2 is a table of crystal data and structure refinement for Compound 17.

FIG. 3A-3C is a table of bond lengths and angles for Compound 17.

DETAILED DESCRIPTION OF THE INVENTION

Figure 1:
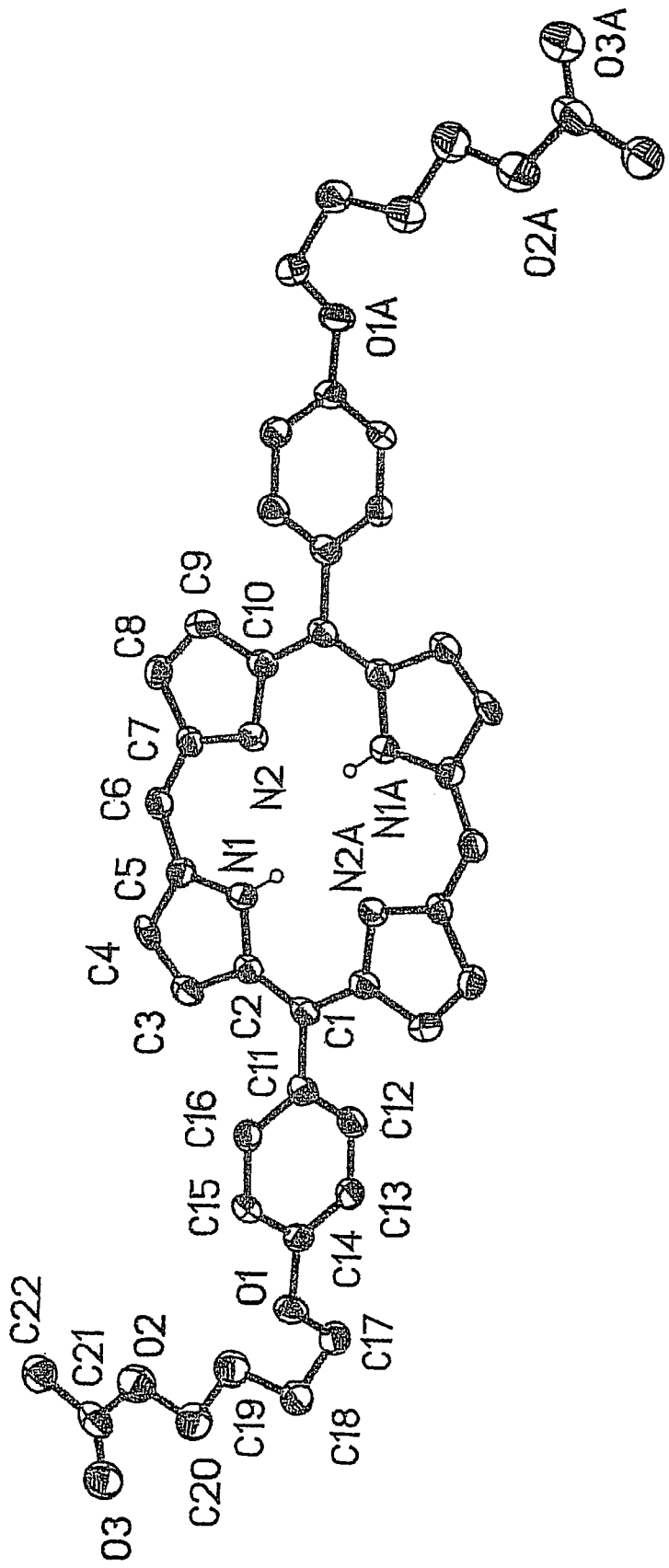
FIG. 1 is a structure drawing of Compound 17.

Aerobic cells generally contain a number of defenses against the deleterious effects of oxyradicals and their reaction products. Superoxide dismutases (SODs) catalyze the reaction:

$$2O_2.^- + 2H^+ \rightarrow O_2 + H_2O_2$$

which removes superoxide and forms hydrogen peroxide. $H_2O_2$ is not a radical, but it is toxic to cells. It is removed by the enzymatic activities of catalase or glutathione peroxidase (GSH-Px). Catalase catalyzes the reaction:

$$2H_2O_2 \rightarrow 2H_2O + O_2$$

thereby removing hydrogen peroxide and forming water and oxygen. GSH-Px removes hydrogen peroxide by using it to oxidize reduced glutathione (GSH) into oxidized glutathione (GSSG) according to the following reaction:

$$2GSH + H_2O_2 \rightarrow GSSG + 2H_2O$$

Other enzymes, such as phospholipid hydroperoxide glutathione peroxidase (PLOOH-GSH-Px), convert reactive phospholipid hydroperoxides, free fatty acid hydroperoxides, and cholesterol hydroperoxides to corresponding harmless fatty acid alcohols. Glutathione S-transferases also participate in detoxifying organic peroxides. In the absence of these enzymes and in presence of transition metals, such as iron or copper, superoxide and hydrogen peroxide can participate in the following reactions which generate the extremely reactive hydroxyl radical HO.:

$$O_2.^- + Fe^{3+} \rightarrow O_2 + Fe^{2+}$$

$$H_2O_2 + Fe^{2+} \rightarrow HO. + HO.^- + Fe^{3+}$$

In addition to enzymatic detoxification of free radicals and oxidant species, a variety of low molecular weight antioxidants such as glutathione, ascorbate, tocopherol, ubiquinone, bilirubin, and uric acid serve as naturally-occurring physiological antioxidants (Krinsky, N I (1992) *Proc. Soc. Exp. Biol. Med.* 200: 248-54). Carotenoids are another class of small molecule antioxidants that have been implicated as protective agents against oxidative stress and chronic diseases. Canfield et al. (1992) *Proc. Soc. Exp. Biol Med.* 200: 260 summarize reported relationships between such carotenoids and various chronic diseases, including coronary heart disease, cataracts, and cancer. Carotenoids have also been shown to dramatically reduce the incidence of certain premalignant conditions, such as leukoplakia, in some patients.

In an effort to prevent the damaging effects of oxyradical formation during reoxygenation of ischemic tissues, a variety of antioxidants have been used. One strategy for preventing oxyradical-induced damage is to inhibit the formation of oxyradicals such as superoxide. Iron ion chelators, such as desferrioxamine (also called deferoxamine or Desferal) and others, inhibit iron ion-dependent HO. generation and thus act as inhibitors of free radical formation (Gutteridge et al. (1979) *Biochem. J.* 184: 469; Halliwell B (1989) *Free Radical Biol. Med.* 7: 645; Van der Kraaij et al. (1989) *Circulation* 80: 158). Amino-steroid-based antioxidants such as the 21-aminosteroids termed "lazaroids" (e.g, U74006F) have also been proposed as inhibitors of oxyradical formation. Desferrioxamine, allopurinol, and other pyrazolopyrimidines such as oxypurinol, have also been tested for preventing oxyradical formation in a myocardial stunning model system (Bolli et al. (1989) *Circ. Res.* 65: 607) and following hemorrhagic and endotoxic shock (DeGarvilla et al. (1992) *Drug Devel. Res.* 25: 139). However, each of these compounds has notable drawbacks for therapeutic usage. For example, deferoxamine is not an ideal iron chelator and its cellular penetration is quite limited.

Another strategy for preventing oxyradical-induced damage is to catalytically remove oxyradicals such as superoxide once they have been formed. Superoxide dismutase and catalase have been extensively explored, with some success, as protective agents when added to reperfusates in many types of experiments or when added when ischemia is imminent (reviewed in Gutteridge *JMC* and Halliwell B (1990) op.cit.). The availability of recombinant superoxide dismutase has allowed more extensive evaluation of the effect of administering SOD in the treatment or prevention of various medical conditions including reperfusion injury of the brain and spinal cord (Uyama et al. (1990) *Free Radic. Biol. Med.* 8: 265; Lim et al. (1986) *Ann. Thorac. Surg.* 42: 282), endotoxemia (Schneider et al. (1990) *Circ. Shock* 30: 97; Schneider et al. (1989) *Prog. Clin. Biol. Res.* 308: 913), myocardial infarction (Patel et al. (1990) *Am. J. Physiol.* 258: H369; Mehta et al. (1989) *Am. J. Physiol.* 257: H1240; Nejima et al. (1989) *Circulation* 79: 143; Fincke et al. (1988) *Arzneimittelforschung* 38: 138; Ambrosio et al. (1987) *Circulation* 75: 282), and osteoarthritis and intestinal ischemia (Vohra et al. (1989) *J. Pediatr. Surg.* 24: 893; Flohe L. (1988) *Mol. Cell. Biochem.* 84: 123). Superoxide dismutase also has been reported to have positive effects in treating systemic lupus erythematosus, Crohn's disease, gastric ulcers, oxygen toxicity, burned patients, renal failure attendant to transplantation, and herpes simplex infection.

An alternative strategy for preventing oxyradical-induced damage is to scavenge oxyradicals such as superoxide once these have been formed, typically by employing small molecule scavengers which act stoichiometrically rather than catalytically. Congeners of glutathione have been used in various animal models to attenuate oxyradical injury. For example, N-2-mercaptopropionylglycine has been found to confer protective effects in a canine model of myocardial ischemia and reperfusion (Mitsos et al. (1986) *Circulation* 73: 1077). N-acetylcysteine ("Mucomyst") has been used to treat endotoxin toxicity in sheep (Bernard et al. (1984) *J. Clin. Invest.* 73: 1772). Dimethyl thiourea (DMTU) and butyl-α-phenylnitrone (BPN) are believed to scavenge the hydroxyl radical, HO., and have been shown to reduce ischemia-reperfusion injury in rat myocardium and in rabbits (Vander Heide et al. (1987) *J. Appl. Physiol.* 63: 2426). Mannitol has also been used as a free radical scavenger to reduce organ injury during reoxygenation (Fox RB (1984) *J. Clin. Invest.* 74: 1456; Ouriel et al. (1985) *Circulation* 72: 254).

Thus, application of inhibitors of oxyradical formation and/or enzymes that remove superoxide and hydrogen peroxide and/or small molecules that act as oxyradical scavengers have all shown promise for preventing re-oxygenation damage present in a variety of ischemic pathological states and for treating or preventing various disease states associated with free radicals. However, the molecular constituents of each of these categories exhibit a number of deleterious properties. For example, inhibitors of oxyradical formation typically chelate transition metals which are used in essential enzymatic processes in normal physiology and respiration; moreover, even at very high doses, these inhibitors do not completely prevent oxyradical formation. Superoxide dismutases and catalase are large polypeptides which are expensive to manufacture, do not penetrate cells or the blood-brain barrier, and generally require parenteral routes of administration. Free radical scavengers act stoichiometrically and are thus easily depleted and must be administered in high dosages to be effective. There are other strong limitations for the use of recombinant metalloenzymes in therapy including solution instability, limited cellular accessibility, immunogenicity, short half-lives, genotoxicity, cost of production and proteolytic digestion.

The complex formed between the chelator desferrioxamine and manganese has SOD activity and has shown some activity in biological models but the instability of the metal ligand complex apparently precludes its pharmaceutical use. The metal ligand must be strictly inserted within the ligand to avoid any demetallation and trapping by serum proteins, especially ceruloplasmin and albumin.

The cationic metalloporphyrins synthesized by Fridovich et al., (*Inorg. Chem.* 38: 4011-4022, (1999)) are SOD mimics. Of these 5, 10, 15, 20 meso-tetrakis(4-methylpyridiniumyl) porphyrinato-manganese (III), (Mn-TMPyP), is also a powerful oxidative DNA cleaver, able to generate DNA damage at nanomolar concentrations (Bernadou et al., *Biochemistry*, 28:7268-7275 (1989), Vialas, C. et al, *J. Am. Chem. Soc.*, 122: 2157-2167 (2000), Meunier, B., *Chem Rev,* 92:1411-1456 (1992)).

The compounds described herein can be non-genotoxic compounds. A genotoxic compound is able to cause damage to double-stranded DNA and compounds can be compared to a reference. Known DNA cleavers such as Bleomycin, an anticancer agent, is a typical reference.

An orally introduced compound of the present invention becomes bioavailable by passing from the lumen of the alimentary canal to the bloodstream of said individual.

A compound of the present invention has a molecular weight of less than about 1000 daltons. In certain embodiments, the compounds have a molecular weight of less than about 600 daltons. And in other embodiments, the compounds have a molecular weight of between about 400 daltons and about 600 daltons, or between about 400 daltons and about 1000 daltons.

The present invention relates to the discovery of low molecular weight compounds which are synthetic non-genotoxic, reactive oxygen species scavengers. These compounds offer a significant advantage, compared to known reactive oxygen scavenger compounds currently in use, due to their water solubilities, low molecular weights, oral bioavailability, metal entrapment caging effects, longer half lives, and non-genotoxic properties.

In one embodiment, the invention relates to compounds represented by Structural Formula I:

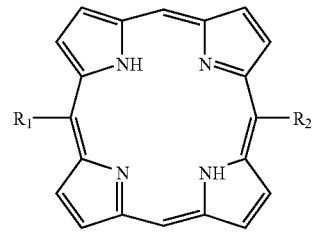

Structural Formula I wherein R1 and R2 are each independently aliphatic groups, lower alkyl, cycloalkyl, halogen substituted alkyl, substituted phenyl groups or unsubstituted phenyl groups. In one embodiment, R1 and R2 are cyclopropyl groups.

In certain embodiments, Structural Formula I is a complex containing a metal ion, such as a first row transition metal such as manganese, iron, cobalt, copper, nickel and zinc. In certain embodiments the metal is iron or manganese.

An aliphatic group is a straight chained, branched or cyclic (non-aromatic) hydrocarbon which is completely saturated or which contains one or more units of unsaturation. Typically, a straight chained or branched aliphatic group has from one to about twenty carbon atoms, preferably from one to about ten, and a cyclic aliphatic group has from three to about eight ring carbon atoms. As aliphatic group as used herein has from three to about eight ring carbon atoms. An aliphatic group is preferably a straight chained or branched alkyl group, e.g., methyl, ethyl, n-propyl, iso-propyl, n-butyl, sec-butyl, pentyl, hexyl, pentyl, or octyl, or a cycloalkyl group with three to about eight ring carbon atoms. For the purposes of the present invention, the term "alkyl" refers to a straight chain or branched hydrocarbon group. An aryl group as used herein refers to unsubstituted and substituted aromatic hydrocarbons, such as phenyl or benzyl groups. Halo is, for example, fluoro, chloro, bromo, iodo; preferably it is fluoro, chloro or bromo.

In certain embodiments, the compounds of the invention form a complex with a counter monovalent anion Y. The counter monovalent anion Y can represent any suitable anion with which the complex of Structural Formula I, Structural Formula II, Structural Formula III and Structural Formula IV can be formed. Suitable examples include chloride, hydroxide and acetate or a pharmaceutically acceptable counter anion. In certain embodiments, the anion is acetate.

In other embodiments, the invention relates to compounds represented by Structural Formula II:

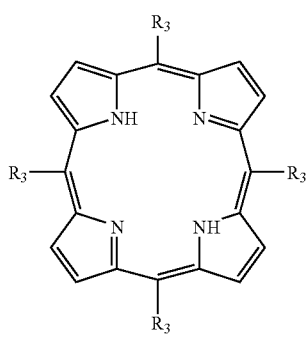

Structural Formula II wherein $R_3$ is an aliphatic group, lower alkyl, cycloalkyl, and halogen substituted alkyl groups.

In certain embodiments, the compound is a complex with a first row transition metal ion such as manganese, iron, cobalt, copper, nickel and zinc.

In certain embodiments, $R_3$ is cyclopropyl. The invention also relates to pharmaceutical formulations comprising one or more pharmaceutically acceptable carriers, diluents or excipients and a therapeutically effective amount of a compound of Structural formula II. In certain aspects, the pharmaceutical formulation comprises Structural Formula II wherein $R_3$ is cyclopropyl. The invention also relates to methods of administering a pharmaceutically effective porphyrin compound to an individual in need thereof, comprising orally introducing a compound of Structural Formula II into said individual wherein said compound becomes bioavailable by passing from the lumen of the alimentary canal to the bloodstream of said individual. In certain embodiments, compound reduces oxyradical- or reactive oxygen-induced damage to cells of said individual as a consequence of said compound becoming bioavailable.

The invention further relates to compounds represented by Structural Formula III:

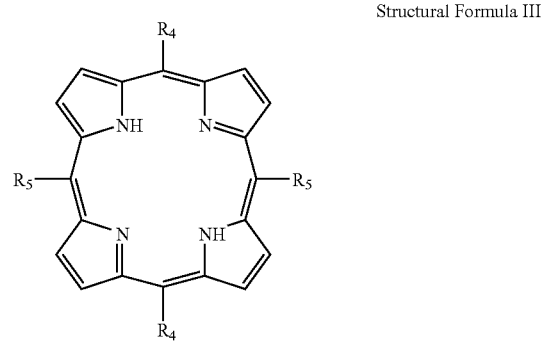

Structural Formula III wherein $R_4$ is an aliphatic group, lower alkyl, halogen substituted alkyl, cycloalkyl or substituted or unsubstituted phenyl group and $R_5$ is lower alkyl, halogen substituted alkyl or cycloalkyl group, further wherein $R_4$ and $R_5$ are not the same. In certain aspects, the compound of Structural Formula III is a complex with a first row transition metal ion such as manganese, iron, cobalt, copper, nickel and zinc.

In certain aspects, the invention relates to compounds of Structural Formula III wherein $R_4$ is cyclopropyl and $R_5$ is a lower alkyl, halogen substituted alkyl or cycloalkyl group. In other embodiments, the compounds are in a complex with a transition metal ion selected from the group consisting of manganese, iron, cobalt, copper, nickel and zinc.

The invention also relates to pharmaceutical formulations comprising one or more pharmaceutically acceptable carriers, diluents or excipients and a therapeutically effective amount of at least one compound of Structural Formula III.

In other embodiments, the pharmaceutical composition comprises Structural Formula III wherein $R_4$ is cyclopropyl and $R_5$ is a lower alkyl, halogen substituted alkyl or cycloalkyl group. The invention also relates to methods of administering a pharmaceutically effective porphyrin compound to an individual in need thereof, comprising orally introducing a compound Structural Formula III into an individual wherein the compound becomes bioavailable by passing from the lumen of the alimentary canal to the bloodstream of the individual. In other embodiments, the compound reduces oxyradical- or reactive oxygen-induced damage to cells of the individual as a consequence of said compound becoming bioavailable.

The invention further relates to compounds represented by Structural Formula IV:

Structural Formula IV

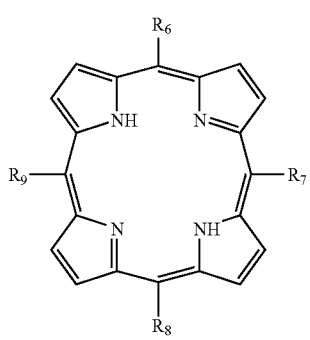

wherein R6, R7 and R8 are each independently hydrogen, lower alkyl, halogen substituted alkyl, cycloalkyl or substituted or unsubstituted phenyl groups and R9 is a lower alkyl, halogen substituted alkyl, cycloalkyl or substituted or unsubstituted phenyl group wherein the groups at positions R6, R7, R8 and R9 are not all the same and R6 and R8 cannot be the same when R7 and R9 are the same. In certain embodiments, the compound is a complex with a first row transition metal ion, such as manganese, iron, cobalt, copper, nickel and zinc.

In other embodiments, R6, R7 and R8 of Structural Formula IV are hydrogen or lower alkyl groups and R9 is cyclopropyl. In certain aspects, the compound is a complex with a transition metal ion such as manganese, iron, cobalt, copper, nickel and zinc.

In other embodiments, R6, is hydrogen and R7, R8 and R9 of Structural Formula IV are cyclopropyl groups. In certain aspects of the invention, the compound is a complex with a transition metal ion such as manganese, iron, cobalt, copper, nickel and zinc.

In certain embodiments there is provided a ligand of the compounds of the invention defined above and selected from the group consisting of:

{[{(Porphine-5,15-diyl)bis[cyclopropyl-diyl]}](2-)-N21, N22, N23, N24}manganese(III)acetate, {[Diethyl-4,4'-{(Porphine-5,15-diyl)bis[benzene-1,4-diyl(oxy)]}bis (butanoato)](2-)-$N^{21},N^{22},N^{23},N^{24}$}manganese(III) acetate,{[{(Porphine-5,15-diyl)bis[benzene-1,4-diyl (oxy)]}bis(butanoic acido)](2-)-$N^{21},N^{22},N^{23}, N^{24}$}manganese(III)acetate, Synthesis of {[(Porphine-5,15-diyl)bis[Methyl 4-benzoate-1,4-diyl]}](2-)-$N^{21}, N^{22},N^{23},N^{24}$}manganese(III)acetate, 4-(3-Hydroxypropyloxy)benzaldehyde,{(21H,23H-Porphine-5,15-diyl)bis[benzene-1,4-diyl(4-[3-(2,3,4,6-Tetra-O-acetyl-β-D-glucosyloxy)propyl-oxy)]}, {{(Porphine-5,15-diyl)bis[benzene-1,4-diyl(4-[3-(2,3, 4,6-Tetra-O-acetyl-β-D-glucosyloxy)propyl-oxy)]} (2-)-$N^{21},N^{22},N^{23},N^{24}$}manganese(III)acetate, {{(Porphine-5,15-diyl)bis[benzene-1,4-diyl(oxy)] butylacetate}(2-)-$N^{21},N^{22},N^{23},N^{24}$}manganese(III)acetate, {[{Porphine-5.15-diyl)bis[benzyl-diyl]}](2-) $N^{21}N^{22},N^{23},N^{24}$}manganese(III)acetate, {[{Porphine-5.15-diyl)bis[benzyl-diyl]}](2-)$N^{21}N^{22},N^{23}, N^{24}$}manganese(III)acetate, (5,10,15,20-Tetraisopropylporphyrinato)manganese(III)acetate, (5,10,15,20-Tetraethylporphyrinato)manganese(III)acetate, (5,10,15,20-Tetramethylporphyrinato)manganese (III)acetate, and {[{Porphine-5.15-diyl)bis[methyl-diyl]}](2-)$N^{21},N^{22},N^{23},N^{24}$}manganese(III)acetate.

While it is possible for the compounds of the present invention to be administered as the complex per se, it is preferred to present the compounds or the complexes in the form of a pharmaceutical formulation.

Pharmaceutical formulations can be adapted for administration by any appropriate route, for example by the oral (including buccal or sublingual), rectal, nasal, topical (including buccal, sublingual or transferal), vaginal or parenteral (including subcutaneous, intramuscular, intravenous or intradermal) route. Such formulations can be prepared by any method known in the art of pharmacy, for example by bringing into association the active ingredient with the carrier(s), diluent(s) or excipient(s).

Thus, according to a further aspect of the present invention there is provided a pharmaceutical formulation comprising at least one compound of Structural Formula I, Structural Formula II, Structural Formula III, and Structural Formula IV together with one or more pharmaceutically acceptable carriers, diluents or excipients.

Pharmaceutical formulations may be presented in unit dose forms containing a predetermined amount of active ingredient per unit dose. Such a unit may contain for example 1 μg to 10 μg, such as 0.01 mg to 1000 mg, or 0.1 mg to 250 mg, of a compound of Structural Formula I, Structural Formula II, Structural Formula III or Structural Formula IV depending on the condition being treated, the route of administration and the age, weight and condition of the patient.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. Typically, tablet or capsules will be prepared to contain from 1 mg to 1000 mg, such as 2.5 mg to 250 mg of active ingredient per unit dose.

Pharmaceutical formulations adapted for transferal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas; rectal ointments and foams may also be employed.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurized aerosols, nebulizers or insufflators. Spray compositions may, for example, be formulated as aerosols delivered from pressurized packs, such as a metered dose inhaler, with the use of a suitable liquified propellant. Capsules and cartridges for use in an inhaler or insufflator, for example gelatine, may be formulated containing a powder mix for inhalation of a compound of the invention and a suitable powder base such as lactose or starch. Each capsule or cartridge may generally contain between 1 μg-10 mg of the compound of Structural Formula I, Structural Formula II, Structural Formula III and Structural Formula IV or combinations thereof. Aerosol formulations are preferably arranged so that each metered dose or "puff" of aerosol contains 1 μg-2000 μg, such as about 1 μg-500 μg a compound of Structural Formula I, Structural Formula II, Structural Formula III and Structural Formula IV or combinations thereof. Administration may be once daily or several times daily, for example 2, 3, 4 or 8 times, giving for example 1, 2 or 3 doses each time. The overall daily dose with an aerosol will generally be within the range 10 μg-10 mg, such as 100 μg-2000 μg. The overall daily dose and the metered dose delivered by capsules and cartridges in an inhaler or insufflator will generally be double those with aerosol formulations.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain the antioxidants as well as buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species ($O_2.^-$, $H_2O_2$, HO., HOCl, ferryl, peroxyl, peroxynitryl, and alkoxyl), or by preventing their formation, or by catalytically converting the free radical or other reactive oxygen species to a less reactive species. An antioxidant compound of the present invention generally has detectable SOD, CAT and/or POD activity. A compound of the present invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. The relative amount of free radical species is often determined by detection of a secondary indicator (e.g., an oxidized substrate; peroxidized lipid, cytochrome C).

As used herein, "free radical-associated diseases or conditions" refers to a pathological condition of an individual that results at least in part from the production of or exposure to free radicals, particularly oxyradicals, and other reactive oxygen species in vivo. Most pathological conditions are multifactorial, in that multiple factors contributing to the disease state are present, and that assigning or identifying the predominant causal factor(s) for any individual pathological condition is frequently extremely difficult. For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g., SOD, catalase) is shown to produce a detectable benefit by decreasing symptoms, increasing survival, or providing other detectable clinical benefits in treating or preventing the pathological state. For example, but not in limitation, the following disease states discussed herein are considered free radical-associated diseases: ischemic reperfusion injury, inflammatory diseases, systemic lupus erythematosus, myocardial infarction, stroke, traumatic hemorrhage, spinal cord trauma, Crohn's disease, autoimmune diseases (e.g., rheumatoid arthritis, diabetes), cataract formation, uveitis, emphysema, gastric ulcers, oxygen toxicity, neoplasia, undesired cell apoptosis, radiation sickness, and other pathological states discussed above, such as toxemia and acute lung injury. Such diseases can include "apoptosis-related ROS" which refers to reactive oxygen species (e.g., $O_2.^-$, HOOH) which damage critical cellular components (e.g., lipid peroxidation) in cells stimulated to undergo apoptosis. Such apoptosis-related ROS may be formed in a cell in response to an apoptotic stimulus and/or produced by non-respiratory electron transport chains (i.e., other than ROS produced by oxidative phosphorylation).

The compounds of Structural Formula I, Structural Formula II, Structural Formula III and Structural Formula IV have antioxidant and/or free radical scavenging properties as demonstrated hereinafter by their SOD, CAT or POD mimetic activity.

The present invention thus also provides compounds of Structural Formula I, Structural Formula II, Structural Formula III and Structural Formula IV for use in medical therapy. The compounds of the present invention are of potential utility in treating and preventing free radical associated diseases and conditions which involve a component of oxidative stress including, for example, Alzheimer's disease, dementia, Parkinson's disease, Lou Gehrig's disease, motor neuron disorders, Huntington's disease, cancer, multiple sclerosis, systemic lupus erythematosus, scleroderma, eczema, dermatitis, delayed type hypersensitivity, psoriasis, gingivitis, adult respiratory distress syndrome, septic shock, multiple organ failure, asthma, allergic rhinitis, pneumonia, emphysema, chronic bronchitis, AIDS, inflammatory bowel disease, pancreatitis, transplantation rejection, atherosclerosis, hypertension, congestive heart failure, myocardial ischemic disorders, angioplasty, endocarditis, retinopathy of prematurity, cataract formation, uveitis, rheumatoid arthritis, osteoarthritis and aging.

In preferred embodiments, the compounds of the present invention and formulations thereof may be used for preventing, arresting, or treating (1) neurological damage such as Parkinson's disease or Alzheimer's disease, (2) cardiac tissue necrosis resulting from cardiac ischemia, (3) autoimmune neurodegeneration (e.g., encephalomyelitis), (4) acute lung injury such as in sepsis and endotoxemia, and (5) neuronal damage resulting from ischemia (e.g., stroke, drowning, brain surgery) or trauma (e.g., concussion or cord shock).

The compounds of the present invention and formulations thereof also have utility for the following additional indications: (1) for preventing ischemic/reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens and (6) for prophylactic administration to prevent carcinogenesis, cellular senescence, cataract formation, formation of malondialdehyde adducts, HIV pathology (as described below) and macromolecular crosslinking, such as collagen crosslinking.

The compounds of the present invention and formulations thereof can also be of benefit to patients who are infected with a human immunodeficiency virus (e.g., HIV-1) or who are at risk of becoming infected with a human immunodeficiency virus. The antioxidant compounds of the present invention can prevent or inhibit the induction of HIV-1 replication in CD4+ lymphocytes by tumor necrosis factor (TNF or other inflammatory mediators) and/or prevent damage to or death of CD4+cells as a consequence of HIV-1 infection. Without wishing to be bound by any particular theory of HIV-1 replication or HIV-1 pathogenesis, it is believed that administration of an antioxidant complex can inhibit and/or slow the development of HIV-1 related pathology and/or can reduce the rate of decline of the CD4+lymphocyte population in HIV infected individuals. The antioxidant compounds of the present invention can also inhibit pathology resulting from excessive or inappropriate levels of TNF or other inflammatory mediators, both in AIDS and in other conditions (e.g., septic shock). Frequently, a dosage of about 50 to 5000 mg will be administered to a patient with HIV and/or with excessive or inappropriate levels of TNF, either in single or multiple doses, to reduce or retard the development of pathology and clinical symptoms. Antioxidant compounds of the present invention can be administered therapeutically to treat viral diseases other than HIV.

The compounds of the present invention and formulations thereof can also have utility in enhancing the recovery of skin of a warm-blooded animal from wounds, such as surgical incisions, burns, inflammation or minor irritation due to oxidative damage, etc.

A further aspect of the invention provides a method of prophylaxis or treatment of a human or animal subject suffering from a disease or condition, which involves a component of oxidative stress and/or a free radical-associated condition, comprising the administration to said subject of, an effective amount of a compound of Structural Formula I, Structural Formula II, Structural Formula III or Structural Formula IV A further aspect of the present invention provides the use of a compound of Structural Formula I, Structural Formula II, Structural Formula III and Structural Formula IV in the preparation of a medicament for the prophylaxis or treatment of a disease or condition which involves a component of oxidative stress and/or a free radical-associated disease or condition.

A further aspect of the present invention provides the use of a compound of Structural Formula I, Structural Formula II, Structural Formula III and Structural Formula IV in the preparation of a medicament for the prophylaxis or treatment of the specific disorders and conditions referred to above.

The compounds of the present invention and formulations thereof can be administered for prophylactic and/or therapeutic treatments. In therapeutic application, formulations are administered to a patient already affected by the particular free radical associated disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 µg to about 10 g of antioxidant compounds of the present invention per dose, with dosages of from 0.1 mg to 2000 mg per patient being more commonly used.

In prophylactic applications, formulations containing the antioxidant compound of the present invention or cocktails thereof are administered to a patient not already in a disease state to enhance the patient's resistance or to retard the progression of disease. Such an amount is defined to be a "prophylactically effective dose." In this use, the precise amounts again depend upon the patient's state of health and general level of immunity, but generally range from 1 µg to 10 g per dose, especially 0.01 mg to 1000 mg per patient.

As indicated above, a typical formulation of a compound of the present invention will contain between about 0.1 and 250 mg of the complex in a unit dosage form. Single or multiple administrations of the formulations can be carried out with dose levels and dosing pattern being selected by the treating physician.

In general, for treatment of free radical-associated diseases, a suitable effective dose of the antioxidant compound of the present invention will be in the range of 0.01 microgram (µg) to 1000 milligram (mg) per kilogram (kg) of body weight of recipient per day, such as in the range of 0.1 µg to 100 mg per kg of body weight per day, for example in the range of 1 µg to 10 mg per kg of body weight per day. For example, 0.2 mg/kg for a 70 kg human adult would result in a daily dose of 14 mg. The desired dosage is presented in one, two, three, four or more subdoses administered at appropriate intervals throughout the day. These subdoses can be administered in unit dosage forms as referred to above.

Kits can also be supplied which contain the compounds of the present invention for use in the protection against or therapy for a free radical-associated disease. Thus, the subject formulation of the present invention may be provided, usually in a lyophilized form or aqueous solution, in a container, either alone or in conjunction with additional antioxidant compounds of the present invention of the desired type. The antioxidant compounds are included in the kits with buffers, such as Tris, phosphate, carbonate, etc., stabilizers, biocides, inert proteins, e.g. serum albumin, or the like, and a set of instructions for use. Generally, these materials will be present in less than about 5% wt. based on the amount of antioxidant compounds of the present invention and usually present in total amount of at least about 0.001% based again on the concentration. Frequently, it will be desirable to include an inert extender or excipient to dilute the active ingredients, where the excipient may be present in from about 1 to 99.999% wt. of the total formulation.

The compounds of the present invention may be employed alone or in combination with other therapeutic agents for the treatment of the above-mentioned conditions, and in particular in combination with other antioxidant agents that have SOD activity, catalase activity, peroxidase activity, or are free radical scavengers or inhibitors of free radical formation. Combination therapies according to the present invention thus comprise the administration of at least one compound of Structural Formula I, Structural Formula II, Structural Formula III and Structural Formula IV or a pharmaceutically acceptable derivative(s) thereof and at least one other pharmaceutically active agent. The compound(s) of Structural Formula I, Structural Formula II, Structural Formula III and Structural Formula IV or a pharmaceutically acceptable derivative(s) thereof and the other pharmaceutically active agent(s) may be administered together or separately and, when administered separately, the respective administrations may occur simultaneously or sequentially in any order. The amounts of the compound(s) of Structural Formula I, Structural Formula II, Structural Formula III and Structural Formula IV or pharmaceutically acceptable derivative(s) thereof and the other pharmaceutically active agent(s) as well as the relative timings of administration will be selected in order to achieve the desired combined therapeutic effect.

Certain embodiments of the present invention will now be illustrated by way of example only. The physical data given for the compounds exemplified is consistent with the assigned structure of those compounds.

Exemplification

In the following synthesis examples, all used chemicals were of reagent grade and purchased from Aldrich (Milwaukee, Wis.) or Acros Organics (Geel, Belgium). Column chromatography was carried out on silica gel 60 AC.C (6-35 μm) from SDS, or basic alumina 90 (70-230 mesh) from Merck (Whitehouse Station, N.J.). Elementary analyses were carried out by the "Service de Microanalyse du Laboratoire de Chimie de Coordination du CNRS". The nuclear magnetic resonance spectra were recorded on a Bruker AMX 300 or AM 250 A or a Bruker AC 200 spectrometer. UV-visible spectra were obtained on Hewlett Packard 8452A diode array spectrophotometer. The mass spectra were recorded on a Nermag R10-10H for the FAB+ spectra and on a API 365 PE SCIEX for the electrospray spectra. Infrared spectra were recorded on a Perkin-Elmer 1725X FT-IR Spectrometer.

Synthesis of dipyrromethane 1

Prepared according to the Lindsey method (Littler B. J., Miller M. A, Hung C.-H., Wagner R. W., O'Shea D. F., Boyle P. D. and Lindsey J. S., *J. Org. Chem.* 64: 1391-1396 (1999).

Synthesis of {(21H,23H-Porphine-5,15-diyl)bis[cyclopropyl-diyl]} 2

Dipyrromethane (1) (1.45 g, 9.93 mmol) and cyclopropanecarboxaldehyde (0.74 mL, 9.93 mmol) were dissolved in 1800 mL of $CH_2Cl_2$. 60 drops of trifluoroacetic acid were added at room temperature and the mixture was stirred overnight under nitrogen atmosphere. 9.76 g of 3,9 mmol tetrachloro-p-benzoquinone (9.76 g, 3.9 mmol) was added and the mixture refluxed for 0.5 h. Solvents were removed and the dark residue was adsorbed onto basic alumina. The compound was then eluted from the basic alumina column using $CH_2Cl_2$ 100%. The dark purple layer was removed and controlled by UV. This operation was repeated until to obtain quinone free porphyrin. The solvents were removed to give a dark purple powder identified as 21H,23H-Porphine-5,15-diyl)bis[cyclopropyl-diyl] (2): 0.43 g (22% Yield). UV-visible ($CH_2Cl_2$) λ (ε $mol^{-1}$ L $cm^{-1}$): 406 (179×10$^3$), 504 (4.9×10$^3$), 536 (1.8×10$^3$), 580 (1.8×10$^3$). $^1$H NMR ($CDCl_3$ at 298K) δ: −2.95 (s, 2H, NH), 1.75 (d, J=4.5 Hz, 4H, $CH_2$), 1.96 (d, J=8.2 Hz, 4H, $CH_2$), 4.21 (td, J=4.5 Hz, J=8.2 Hz, 2H, CH), 9.35 (d, J=4.5 Hz, 4H, Hβ), 9.92 (d, J=4.5 Hz, 4H, Hβ), 10.13 (s, 2H, Hmeso). Anal.: Calc for $C_{26}H_{22}N_4$.0.6 $CH_2Cl_2$: C, 72.37; H, 5.29; N, 12.69. Found: C, 72.31; H, 5.02; N, 11.35. MS ($DCI/NH_3$), m/z 391 (MH+).

Synthesis of {[{(Porphine-5,15-diyl)bis[cyclopropyl-diyl]}](2-)-$N^{21}$,$N^{22}$,$N^{23}$,$N^{24}$}manganese(III)acetate (3)

1.09 mL (8.25 mmol) of 2,4,6-collidine and 4.04 g (16 mmol) of $Mn(OAc)_2.4H_2O$ was added to a solution of 0.32 g (0.72 mmol) of 21H,23H-Porphine-5,15-diyl)bis[cyclopropyl-diyl (2) in 70 mL of DMF. The mixture was heated at 90° C. during 6 h under nitrogen, cooled to room temperature and 100 mL of water were added. Metallated porphyrin was extracted with 200 mL of $CH_2Cl_2$ and the organic layer was dried over anhydrous sodium sulfate. Solvents were removed under vacuum and the crude product was dissolved in the minimum quantity of $CH_2Cl_2$. A large amount of n-hexane was then added to the solution until to obtain a precipitate. The precipitate was filtered, washed several times with n-hexane leading to a dark powder {[{(Porphine-5,15-diyl)bis[cyclopropyl-diyl]}](2-)-$N^{21}$,$N^{22}$,$N^{23}$,$N^{24}$}manganese(III)acetate 3: 0.19 g (50% yield). UV-visible (MeOH) λ (ε $mol^{-1}$ $cm^{-1}$): 374 (29.2×10$^3$), 394 (26.8×10$^3$), 462 (42.1×10$^3$), 554 (6.4×10$^3$). Anal.: Calc for $C_{21}H_{23}N_4O_2Mn.1.5H_2O$: C, 63.51; H, 4.94; N, 10.58. Found: C, 63.77; H, 4.65; N, 10.55. MS (ES), m/z 443.0 ($C_{26}H_{20}N_4Mn$, z=1).

Synthesis of Ethyl 4-(4-Formylphenoxy)butanoate (4)

Prepared according to Wytko J., Berl V., McLaughlin M., Tykwinski R. R., Schreiber M., Diederich F., Boudon C., Gisselbrecht J.-P. and Gross M. *Helv. Chem. Acta*, 81: 1964-1977 (1998).

Synthesis of Diethyl-4,4'-{(21H,23H-Porphine-5,15-diyl)bis[benzene-1,4-diyl(oxy)]}bis(butanoate) (5)

Prepared according to Wytko J., Berl V., McLaughlin M., Tykwinski R. R., Schreiber M., Diederich F., Boudon C., Gisselbrecht J.-P. and Gross M. *Helv. Chem. Acta*, 81: 1964-1977 (1998).

Synthesis of {[Diethyl-4,4'-{(Porphine-5,15-diyl)bis [benzene-1,4-diyl(oxy)]}bis(butanoato)](2-)-$N^{21}$, $N^{22}$,$N^{23}$,$N^{24}$}manganese(III)acetate 6

0.18 mL (1.38 mmol) of 2,4,6-collidine and 0.67 g (2.76 mmol) of $Mn(OAc)_2.4H_2O$ was added to a solution of 0.10 g (0.13 mmol) of 5 in 10 mL of DMF. The mixture was heated at 90° C. during 4 h under nitrogen atmosphere. Then 50 mL of water were added and a precipitate appeared. This precipitate was filtered, washed with 150 mL of water and 100 mL of diethyl ether leading to a dark powder identified as 6: 0.081 g (67% Yield). UV-visible (MeOH) λ (ε $mol^{-1}$ L $cm^{-1}$): 314 (22.4×10$^3$), 376 (45.6×10$^3$), 396 (46.3×10$^3$), 462 (69.1×10$^3$), 550 (9.8×10$^3$). IR (KBr): v=1733.7 $cm^{-1}$ (C=O). Anal.: Calc for $C_{46}H_{43}N_4O_8Mn.2H_2O$: C, 63.45; H, 5.44; N, 6.43. Found: C, 63.67; H, 5.62; N, 6.42. MS (ES), m/z 775.2 ($C_{44}H_{40}N_4O_6Mn$, z=1).

Synthesis of {[{(Porphine-5,15-diyl)bis[benzene-1, 4-diyl(oxy)]}bis(butanoic acido)](2-)-N²¹,N²²,N²³, N²⁴}manganese(III)acetate 7

0.099 g of KOH was added to a solution of 0.037 g (0.042 mmol) of 6 in 3 mL of Ethanol. The mixture was refluxed 1 h and then diluted solution of HCl was added in water until to obtain the neutrality. The black precipitate which was appeared in the mixture was filtered off to give 0.012 g (35% Yield) of 7. UV-visible (MeOH/DMSO 96:4) $\lambda$ ($\epsilon$ mol$^{-1}$ L cm$^{-1}$): 316 (18.8×10$^3$), 376 (28.5×10$^3$), 396 (28.6×10$^3$), 462 (39.4×10$^3$), 552 (11×10$^3$). IR (KBr): v=1705.0 cm$^{-1}$ (C=O). Anal.: Calc for $C_{42}H_{35}N_4O_8Mn.H_2O$: C, 63.32; H, 4.68; N, 7.03. Found: C, 63.50; H, 4.50; N, 7.25. MS (ES), m/z 719.2 ($C_{40}H_{32}N_4O_6Mn$, z=1).

Synthesis of Methyl 4-Formylbenzoate 8

Prepared according to Sharma et al., Eur. *J. Org. Chem.* 2095-2103 (2000)).

Synthesis of {(21H,23H-Porphine-5,15-diyl)bis[Methyl 4-benzoate-1,4-diyl]} 9

Ten drops of Trifluoroacetic acid were added to a mixture of 0.25 g (1.71 mmol) of 1 and 0.280 g (1.71 mmol) of 8 in 300 mL of CH$_2$Cl$_2$ at room temperature under nitrogen atmosphere. The mixture was stirred overnight and 1.68 g (6.84 mmol) of tetrachloro-p-benzoquinone were added and reaction mixture was refluxed for 1 h. Solvents were then removed and crude product was chromatographied over SiO$_2$ 60 AC.C with CH$_2$Cl$_2$ 100% as eluant. The red layer was collected and dichloromethane was removed under vacuum. The crude was solubilized in minimum quantity of MeOH and precipitated by adding Et$_2$O. Precipitate was filtered and washed by Et$_2$O leading to a purple powder identified as 9: 0.1 g (10% Yield). UV-visible (CH$_2$Cl$_2$) $\lambda$ ($\epsilon$ mol$^{-1}$ L cm$^{-1}$): 408 (105×10$^3$), 502 (5.6×10$^3$), 538 (2.8×10$^3$), 576 (2.7×10$^3$). $^1$H NMR (CDCl$_3$ at 298K) $\delta$: −3.17 (s, 2H, NH), 4.17 (s, 6H, OCH$_3$), 8.39 (d, J=6 Hz, 4H, HAr), 8.52 (d, J=6 Hz, 4H, HAr), 9.06 (d, J=4.5 Hz, 4H, H$\beta$), 9.45 (d, J=4.5 Hz, 4H, H$\beta$), 10.38 (s, 2H, Hmeso). Anal.: Calc for $C_{36}H_{26}N_4O_4.C_6Cl_4O_2$: C, 61.18; H, 3.18; N, 6.80. Found: C, 61.40; H, 3.15, N, 6.77. MS (FAB+/BA), m/z=579 (MH+).

Synthesis of {[(Porphine-5,15-diyl)bis[Methyl 4-benzoate-1,4-diyl]](2-)-N²¹,N²²,N²³, N²⁴}manganese(III)acetate 10

0.20 mL (1.55 mmol) of 2,4,6-collidine and 0.76 g (3.11 mmol) of Mn(OAc)$_2$.4H$_2$O was added to a solution of 0.09 g (0.155 mmol) of 9 in 20 mL of DMF. The mixture was heated at 90° C. during 4 h under nitrogen atmosphere. Then 100 mL of water were added and a precipitate appeared. This precipitate was filtered off, washed by 150 mL of water and 100 mL of diethyl ether leading to a dark powder identified as 10: 0.053 g (67% Yield). UV-visible (MeOH) $\lambda$ ($\epsilon$ mol$^{-1}$ L cm$^{-1}$): 372 (39.1×10$^3$), 394 (36.2×10$^3$), 458 (57.1×10$^3$), 548 (11.8× 10$^3$). IR (KBr): v=1726.8 cm$^{-1}$ (C=O). Anal.: Calc for $C_{38}H_{27}N_4O_6Mn.2H_2O$: C, 62.81; H, 4.30; N, 7.71. Found: C, 62.31; H, 3.27; N, 7.74. MS (ES), m/z 631.1 ($C_{36}H_{24}N_4O_4Mn$, z=1).

Synthesis of {[(Porphine-5,15-diyl)bis[4-benzoic acid-1,4-diyl]](2-)-N²¹,N²²,N²³,N²⁴}manganese(III) acetate 10

0.116 g of KOH was added To a solution of 0.036 g (0.049 mmol) of 9 in 3 mL of Ethanol. The mixture was refluxed 1 h and then diluted solution of HCl in water was added until to obtain pH 3. The black precipitate which was appeared in the mixture was filtered off to give 0.028 g (79% Yield) of 10. UV-visible (MeOH) $\lambda$ ($\epsilon$ mol$^{-1}$ L cm$^{-1}$): 372 (29.8×10$^3$), 394 (27.9×10$^3$), 460 (39.4×10$^3$), 546 (5×10$^3$). IR (KBr): v=1716.2 cm$^{-1}$ (C=O).
Anal.: Calc for $C_{36}H_{23}N_4O_6Mn.3H_2O$: C, 60.34; H, 4.08; N, 7.82. Found: C, 60.04; H, 3.19; N, 7.62. MS (ES), m/z 603.0 ($C_{34}H_{20}N_4O_4Mn$, z=1).

Synthesis of 4-(3-Hydroxypropyloxy)benzaldehyde 11

Prepared according to Gaud O., et al., *G. Can. J. Chem.* 74, 481-499 (1999).

Synthesis of 4-(3-(2,3,4,6-Tetra-O-acetyl-β-D-glucosyloxy)propyl-oxy)benzaldehyde 12

Prepared according to Gaud O., et al., *G. Can. J. Chem.* 74, 481-499 (1999).

Synthesis of {(21H,23H-Porphine-5,15-diyl)bis[benzene-1,4-diyl(4-[3-(2,3,4,6-Tetra-O-acetyl-β-D-glucosyloxy)propyl-oxy)]} 13

Ten drops of Trifluoroacetic acid were added to a mixture of 0.086 g (0.58 mmol) of 1 and 0.3 g (0.58 mmol) of 12 in 100 mL of CH$_2$Cl$_2$ at room temperature under nitrogen atmosphere. The mixture was stirred overnight. Then 0.57 g (2.35 mmol) of tetrachloro-p-benzoquinone were added and reaction mixture was refluxed for 1 h. Solvents were then removed and crude product was chromatographied over SiO$_2$ 60 AC.C with CH$_2$Cl$_2$/MeOH (90:10) as eluant. The red layer was collected and solvents were removed under vacuum. The crude was solubilized in minimum quantity of CH$_2$Cl$_2$ and precipitated by adding n-hexane. Precipitate was filtered off and washed with n-hexane leading to a purple powder identified as 13: 0.2 g (45% Yield). UV-visible (CH$_2$Cl$_2$) $\lambda$ ($\epsilon$ mol$^{-1}$ L cm$^{-1}$): 410 (807×10$^3$), 504 (81.4×10$^3$), 540 (61.9× 10$^3$), 580 (65.5×10$^3$). $^1$H NMR (CDCl$_3$ at 298K) $\delta$: −3.10 (s, 2H, NH), 2.01-2.17 (m, 24H, CH$_3$CO), 2.28 (quint, J=5.8 Hz, 4H, CH$_2$β), 3.76-4.39 (m, 12H, CH$_2$α, CH$_2$γ, H$_6$, H$_5$), 4.65 (d, J=7.7 Hz, 2H, H$_1$), 5.07 (t, J=9.2 Hz, 2H, H$_2$), 5.16 (t, J=10.2 Hz, 2H, H$_4$), 5.29 (t, J=9.3 Hz, 2H, H$_3$), 7.32 (d, J=8.3 Hz, 4H, H$_{3',5'}$), 8.18 (d, J=8.3 Hz, 4H, H$_{2',6'}$), 9.08 (d, J=4.7 Hz, 4H, H$_\beta$), 9.39 (d, J=4.7 Hz, 4H, H$_\beta$), 10.30 (s, 2H, Hmeso). IR (KBr): v=1755.5 cm$^{-1}$ (C=O). Anal.: Calc for $C_{66}H_{70}N_4O_{22}.C_6H_{14}.2CH_2Cl_2$: C, 58.19; H, 5.81; N, 3.67. Found: C, 58.20; H, 5.14; N, 3.09. MS (ES), m/z 1271.4 ($C_{66}H_{71}N_4O_{22}$, z=1), m/z 1293.3 ($C_{66}H_{70}N_4O_{22}Na$, z=1), m/z 1309.4 ($C_{66}H_{70}N_4O_{22}K$, z=1).

Synthesis of {{(Porphine-5,15-diyl)bis[benzene-1,4-diyl(4-[3-(2,3,4,6-Tetra-O-acetyl-β-D-glucosyloxy) propyl-oxy)]}(2-)-N²¹,N²²,N²³,N²⁴}manganese(III) acetate 14

52 µL (0.39 mmol) of 2,4,6-collidine and 0.19 g (0.78 mmol) of Mn(OAc)$_2$.4H$_2$O was added to a solution of 0.05 g (0.033 mmol) of 13 in 5 mL of DMF. The mixture was heated at 100° C. during 2 h under nitrogen atmosphere. Then 50 mL of water were added and the product was extracted with $CH_2Cl_2$. The organic layer was dried over $Na_2SO_4$, filtered and solvents were evaporated by vacuum. Crude was dissolved in minimum quantity of $CH_2Cl_2$ and precipitated by adding n-hexane. After decantation the liquid layer as removed and the precipitate was dried under vacuum leading to a dark powder identified as 14: 0.040 g (80% Yield). UV-visible (MeOH) λ (ε $mol^{-1}$ L $cm^{-1}$): 316 (13.8×10³), 376 (29.2×10³), 394 (29.7×10³), 462 (46.3×10³), 550 (5.4×10³). IR (KBr): v=1750.4 $cm^{-1}$ (C=O). Anal.: Calc for $C_{68}H_{71}N_4O_{24}Mn.5H_2O$: C, 55.44; H, 5.54; N, 3.80. Found: C, 55.47; H, 5.05; N, 3.34. MS (ES), m/z 1323.1 ($C_{66}H_{68}N_4O_{22}Mn$, z=1).

Synthesis of {{(Porphine-5,15-diyl)bis[benzene-1,4-diyl(4-[3-(β-D-glucosyloxy)propyl-oxy)]}(2-)-$N^2$, $N^{22},N^{23},N^{24}$}manganese(III)acetate 15

0.15 mL of a solution of MeONa 1M in methanol was added to a solution of 0.017 g (0.011 mmol) of 14 in 2 mL of $CH_2Cl_2$/MeOH (80:20). The mixture was stirred at room temperature during 1 h and then 100 mL of water were added. Then pH 1 was obtained by adding HCl solution in water and the compound was extracted with n-butanol. Solvents were then evaporated under vacuum. Crude was dissolved in minimum quantity of MeOH and precipitated by adding diethyl ether. Precipitate was washed by ether leading to a dark powder identify as 15: 0.014 g (80% Yield) UV-visible (MeOH) λ (ε $mol^{-1}$ L $cm^{-1}$): 376 (53.6×10³), 396 (53.7×10³), 462 (81.7×10³), 552 (11.8×10³), IR (KBr): v=3435 $cm^{-1}$ (OH). Anal.: Calc for $C_{52}H_{55}N_4O_{16}Mn.9NaCl$: C, 39.71; H, 3.52; N, 3.56. Found: C, 39.91; H, 3.52; N, 3.35. MS (ES), m/z 987.3 ($C_{50}H_{52}, N_4O_{14}Mn$, z=1).

Synthesis of 4-(4-oxybutylacetate)benzaldehyde 16

6.10 g of (50 mmol) of 4-hydroxybenzaldehyde and 10.36 g (75 mmol) were dissolved in 30 mL of DMF and refluxed 15 min. Then 7.42 mL (51 mmol) of 4-bromobutylacetate were added and the mixture was refluxed during 4 h. Product was then extracted with $CH_2Cl_2$, organic layer was dried over $Na_2SO_4$, filtered evaporated and the crude orange product was chromatographed over $SiO_2$ AC.C with $CH_2Cl_2$ 100% as eluant (Rf=0.4). Fractions with 16 were collected and solvents were removed under vacuum leading to a liquid identified as 16: 11.45 g (97% Yield).

$^1$H NMR ($CDCl_3$ at 298K) δ: 1.75-1.91 (m, 4H, $CH_2\beta\gamma$), 2.03 (s, 3H, $CH_3$), 4.05 (t, J=5.8 Hz, 2H, $CH_2\alpha$), 4.12 (t, J=6.0 Hz, 2H, $CH_2\delta$), 6.96 (d, J=8.7 Hz, 2H, HAr), 7.80 (d, J=8.5 Hz, 2H, HAr), 9.85 (s, 1H, CHO). IR (Pure): v=1734 $cm^{-1}$ (C=O Aldehyde, ester)

Synthesis of {(21H,23H-Porphine-5.15-diyl)bis[benzene-1,4-diyl(oxy)] butylacetate} 17

Ten drops of Trifluoroacetic acid were added to a mixture of 0.25 g (1.71 mmol) of 1 and 0.404 g (1.71 mmol) of 17 in 300 mL of $CH_2Cl_2$ at room temperature under nitrogen atmosphere. The mixture was stirred overnight and 1.68 g (6.84 mmol) of tetrachloro-p-benzoquinone were added and reaction mixture was refluxed for 1 h. Solvents were then removed and crude product was chromatographied over $SiO_2$ 60 AC.C with $CH_2Cl_2$ 100% as eluant. The red layer was collected and dichloromethane was removed under vacuum. The crude was solubilized in minimum quantity of MeOH and precipitated by adding $Et_2O$. Precipitate was filtered off and washed by $Et_2O$ leading to a purple powder identified as 17:

0.23 g (18% Yield). UV-visible ($CH_2Cl_2$) λ (ε $mol^{-1}$ L $cm^{-1}$): 410 (208×10³), 504 (16.5×10³), 540 (12.3×10³), 578 (14.3×10³). $^1$H NMR ($CDCl_3$ at 298K) δ: −3.05 (s, 2H, NH), 2.04-2.10 (m, 8H, $CH_2\beta$, $CH_2\gamma$), 2.17 (s, 6H, $CH_3$), 4.30-4.35 (m, 8H, $CH_2\alpha$, $CH_2\delta$), 7.34 (d, J=9 Hz, 4H, $H_{62}$), 8.20 (d, J=9 Hz, 4H, $H_{5,3}$), 9.13 (d, J=6 Hz, 4H, Hβ), 9.41 (d, J=6 Hz, 4H, Hβ), 10.32 (s, 2H, Hmeso). Anal.: Calc for $C_{44}H_{42}N_4O_6.1.5H_2O$: C, 70.47; H, 6.04; N, 7.47. Found: C, 70.06; H, 5.14, N, 7.03. IR (KBr): v=1727.1 (C=O). MS (FAB+/MNBA), m/z=723 (MH+). Slow evaporation of concentrated solution of 17 in $CH_2Cl_2$ allowed suitable crystals for X-Ray analysis. The results of this analysis is depicted in FIG. 1, FIG. 2 and FIG. 3A-3C.

Synthesis of {{(Porphine-5,15-diyl)bis[benzene-1,4-diyl(oxy)] butylacetate}(2-)-$N^{21}$, $N^{22},N^{23}$, $N^{24}$}manganese(III)acetate 18

0.18 mL (1.38 mmol) of 2,4,6-collidine and 0.67 g (2.76 mmol) of $Mn(OAc)_2.4H_2O$ was added to a solution of 0.10 g (0.133 mmol) of 17 in 10 mL of DMF. The mixture was heated at 90° C. during 4 h under nitrogen. The reaction mixture was cooled to room temperature and then 100 mL of water were added. Metallated porphyrin was extracted with 200 mL of $CH_2Cl_2$ and the organic layer was dried over anhydrous sodium sulfate. Solvents were removed under vacuum and the crude product was dissolved in the minimum quantity of $CH_2Cl_2$. A large amount of n-hexane was then added to the solution until to obtain a precipitate. The precipitate was filtered off, washed several times with n-hexane leading to a dark powder 18: 0.047 g (39% yield). UV-visible (MeOH) λ (ε $mol^{-1}$ L $cm^{-1}$): 314 (22.5×10³), 374 (43.4×10³), 396 (43.8×10³), 462 (68.4×10³), 550 (10.4×10³). IR (KBr): v=1736.0 $cm^{-1}$. Anal.: Calc for $C_{46}H_{43}N_4O_8Mn.4H_2O$: C, 60.92; H, 5.67; N, 6.18. Found: C, 60.37; H, 5.27; N, 5.60. MS (ES), m/z 775.2 ($C_{44}H_{40}N_4O_6Mn$, z=1).

Synthesis of {(21H,23H-Porphine-5.15-diyl)bis[benzyl-diyl]} 19

Prepared according to the Manka & Lawrence method (J. S. Manka and D. S. Lawrence, *Tetrahedron Letters*, 30: 6989-6992 (1989)).

Synthesis of {[{Porphine-5.15-diyl)bis[benzyl-diyl]}](2-)$N^{21}N^{22},N^{23},N^{24}$}manganese(III)acetate 20

0.25 g (0.54 mmol) of 19 in 15 mL of DMF was added to 0.71 mL (5.4 mmol) of 2,4,6-collidine and 2.64 g (10 mmol) of $Mn(OAc)_2.4H_2O$. The reaction mixture was heated 2 h under reflux and under nitrogen. 100 mL of $H_2O$ was added to the cooled solution and metallated porphyrin was extracted with 200 mL of $CH_2Cl_2$. The organic layer was dried over sodium sulphate and filtered. Solvents were removed under vacuum and the crude product was dissolved in a minimum quantity of MeOH. A large amount of diethyl ether was then added to obtain a precipitate. The precipitate was filtered off, washed several times with diethyl ether leading to a dark powder 20: 0.031 g (10% Yield). UV-visible (MeOH) λ (ε $mol^{-1}$ L $cm^{-1}$): 372 (32.5×10³), 394 (30.3×10³), 460 (40.4× 10³), 550 (3.7×10³). Anal.: Calc for $C_{34}H_{23}N_4O_2Mn.2.5CH_2Cl_2.C_2H_7NO$: C, 55.17; H, 4.10; N, 8.14. Found: C, 55.63; H, 3.81; N, 8.30. MS (ES), m/z 515.1 ($C_{32}H_{20}N_4Mn$).

Synthesis of 5,10,15,20-Tetraisopropylporphyrin 21

Prepared according to M. O. Senge, et al., K. Smith, *Journal of Porphyrins and Phthalocyanines*, 3, 99-116 (1999).

Synthesis of (5,10,15,20-Tetraisopropylporphyrinato)manganese(III)acetate 22

0.42 mL (3.2 mmol) of 2,4,6-collidine and 1.57 g (6.4 mmol) of Mh(OAc)$_2$.4H$_2$O was added to a solution of 0.15 g (0.32 mmol) of 21 in 25 mL of DMF. The reaction mixture was heated at 90° C. 2 h under nitrogen. 100 mLs of H$_2$O were added to the cooled solution and metallated porphyrin was extracted with 200 mL of CH$_2$Cl$_2$. The organic layer was dried over sodium sulphate and filtered. Solvents were removed under vacuum and the crude product was dissolved in a minimum quantity of CH$_2$Cl$_2$. A large amount of n-hexane was then added to obtain a precipitate. The precipitate was filtered off, washed several times with n-hexane leading to a dark powder 22: 0.047 g (24% Yield). UV-visible (MeOH) λ (ε mol$^{-1}$ L cm$^{-1}$): 320 (21.3×10$^3$), 376 (33.5×10$^3$), 400 (32.2×10$^3$), 416 (31.3×10$^3$), 470 (74.3×10$^3$). 620 (5.5× 10$^3$). Anal.: Calc for C$_{34}$H$_{39}$N$_4$O$_2$Mn.0.75H$_2$O: C, 67.59; H, 6.75; N, 9.27. Found: C, 67.53; H, 5.98; N, 8.70. MS (ES), m/z 531.2 (C$_{32}$H$_{36}$N$_4$Mn).

Synthesis of 5,10,15,20-Tetraethylporphyrin 23

Prepared according to S. Neya, N. Funasaki, *J. Heterocyclic Chem.*, 34, 689-690 (1997)

Synthesis of (5,10,15,20-Tetraethylporphyrinato) manganese(III)acetate 24

A solution of 0.58 g (2.3 mmol) of Mn(OAc)$_2$.4H$_2$O in 50 mL of MeOH was added to a solution of 0.05 g (0.12 mmol) of 23 in 100 mL of CH$_2$Cl$_2$. The reaction mixture under nitrogen was heated 48 h under reflux. Then 100 mL of H$_2$O were added to the cooled solution and metallated porphyrin was extracted with 200 mL of CH$_2$Cl$_2$. The organic layer was dried over sodium sulphate and filtered. Solvents were removed under vacuum and the crude product was dissolved in a minimum quantity of CH$_2$Cl$_2$. A large amount of n-hexane was then added until to obtain a precipitate. The precipitate was filtered off, washed several times with n-hexane leading to a dark powder 24: 0.022 g (36% Yield). UV-visible (MeOH) λ (ε mol$^{-1}$ L cm$^{-1}$): 380 (21.4×10$^3$), 402 (19.2×10$^3$), 422 (23×10$^3$), 472 (29.9×10$^3$), 576 (4.3×10$^3$), 614 (4.9×10$^3$). Anal.: Calc for C$_{30}$H$_{31}$N$_4$O$_2$Mn.0.5CH$_2$Cl$_2$: C, 63.48; H, 5.59; N, 9.70. Found: C, 63.66; H, 4.95; N, 9.21. MS (ES), m/z 461.2 (C$_{28}$H$_{28}$N$_4$Mn).

Synthesis of 5,10,15,20-Tetramethylporphyrin 25

Prepared according to the literature (S. Neya and N. Funasaki, *J. Heterocyclic Chem.*, 34, 689-690 (1997)).

Synthesis of (5,10,15,20-Tetramethylporphyrinato) manganese(III)acetate 26

A solution of 0.67 g (2.7 mmol) of Mn(OAc)$_2$.4H$_2$O in 50 mL of MeOH was added to a solution of 0.05 g (0.13 mmol) of 25 in 100 mL of CH$_2$Cl$_2$. The reaction mixture was heated 8 h under reflux and nitrogen. 100 mLs of H$_2$O were added to the cooled solution and metallated porphyrin was extracted with 200 mL of CH$_2$Cl$_2$. The organic layer was dried over sodium sulphate and filtered. Solvents were removed under vacuum and the crude product was dissolved in a minimum quantity of CH$_2$Cl$_2$. A large amount of n-hexane was then added until to obtain a precipitate. The precipitate was filtered off, washed several times with n-hexane leading to a dark powder 26: 0.039 g (60% Yield). UV-visible (MeOH) λ (ε mol$^{-1}$ L cm$^{-1}$): 344 (18.5×10$^3$), 380 (28×10$^3$), 422 (33.6× 10$^3$), 472 (36.7×10$^3$), 584 (4.8×10$^3$), 620 (6.3×10$^3$). Anal.: Calc for C$_{26}$H$_{23}$N$_4$O$_2$Mn.2CH$_2$Cl$_2$.2.5CH$_3$OH: C, 50.29; H, 5.07; N, 7.69. Found: C, 50.57; H, 4.67; N, 7.03. MS (ES), m/z 419.1 (C$_{24}$H$_{20}$N$_4$Mn).

Synthesis of {(21H,23H-Porphine-5.15-diyl)bis[methyl-diyl]} 27

1.73 g (11 mmol) of 1 and 0.62 mL (11 mmol) of acetaldehyde were dissolved in 2000 mL of CH$_2$Cl$_2$. 68 drops of trifluoroacetic acid were added at room temperature and the mixture was stirred overnight under nitrogen atmosphere. Then 3.74 g (16.5 mmol) of tetrachloro-p-benzoquinone were added and the mixture was refluxed for 1 h and then stirred 2 h at room temperature. The dark solution was filtered on paper and the filtrate was concentrated under vacuum leading to a dark powder identified as 28: 0.266 g (5% Yield). $^1$H NMR (CDCl$_3$, at 298K) δ: 4.70 (s, 6H, CH$_3$), 9.47 (d, J=6 Hz, 4H, Hβ), 9.67 (d, J=6 Hz, 4H, Hβ), 10.21 (s, 2H, Hmeso). UV-visible (CH$_2$Cl$_2$) λ (ε mol$^{-1}$ L cm$^{-1}$): 354 (37.3×10$^3$), 404 (313.5×10$^3$), 504 (18.6×10$^3$), 536 (4.7×10$^3$), 580 (6.2×10$^3$), 636 (2.9×10$^3$). Anal.: Calc for C$_{22}$H$_{18}$N$_4$.1.5CH$_2$Cl$_2$: C, 60.59; H, 4.45; N, 12.02. Found: C, 59.91; H, 4.00; N, 13.06. MS (DCI/NH$_3$), m/z 339 (100%, MH+).

Synthesis of {[{Porphine-5.15-diyl)bis[methyl-diyl]}](2-)N$^{21}$,N$^{22}$,N$^{23}$,N$^{24}$}manganese(III) acetate 28

A solution of 1.45 g (5.9 mmol) of Mn(OAc)$_2$.4H$_2$O in 100 mL of MeOH was added to a solution of 0.10 g (0.21 mmol) of 27 in 200 mL of degassed CH$_2$Cl$_2$. The reaction mixture under nitrogen was heated 48 h under reflux. 100 mLs of H$_2$O were added to the cooled solution and metallated porphyrin was extracted with 200 mL of CH$_2$Cl$_2$. The organic layer was dried over sodium sulphate and filtered. Solvents were removed under vacuum and the crude product dissolved in a minimum quantity of CH$_2$Cl$_2$. A large amount of n-hexane was added to obtain a precipitate. The precipitate was filtered, washed several times with n-hexane leading to a dark powder 28: 0.019 g (12% Yield). UV-visible (MeOH) λ (ε mol$^{-1}$ L cm$^{-1}$): 374 (60.6×10$^3$), 394 (53.9×10$^3$), 462 (71.2×10$^3$), 554 (11.6×10$^3$). Anal.: Calc for C$_{24}$H$_{19}$N$_4$O$_2$Mn.1.25CH$_2$Cl$_2$: C, 54.49; H, 3.89; N, 10.06. Found: C, 54.03; H, 3.30; N, 10.52. MS (ES), m/z 390.9 (C$_{22}$H$_{16}$N$_4$Mn).

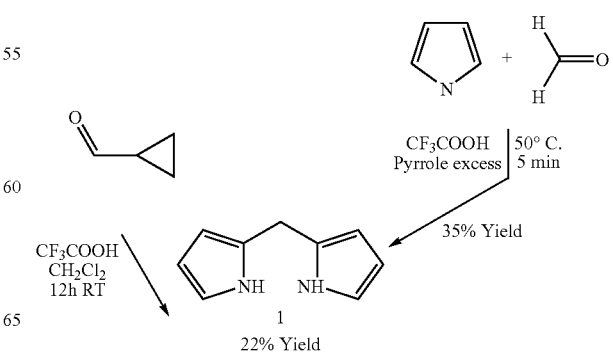

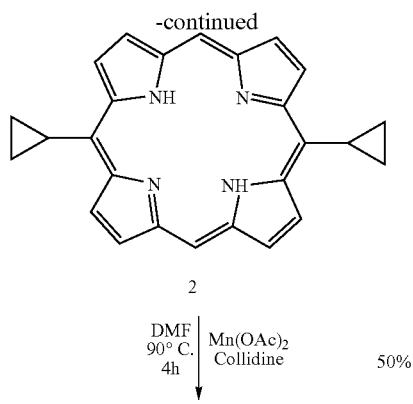
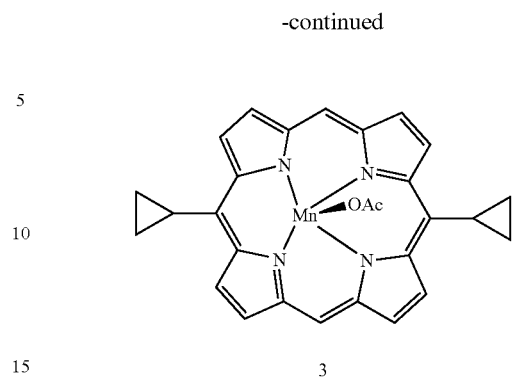
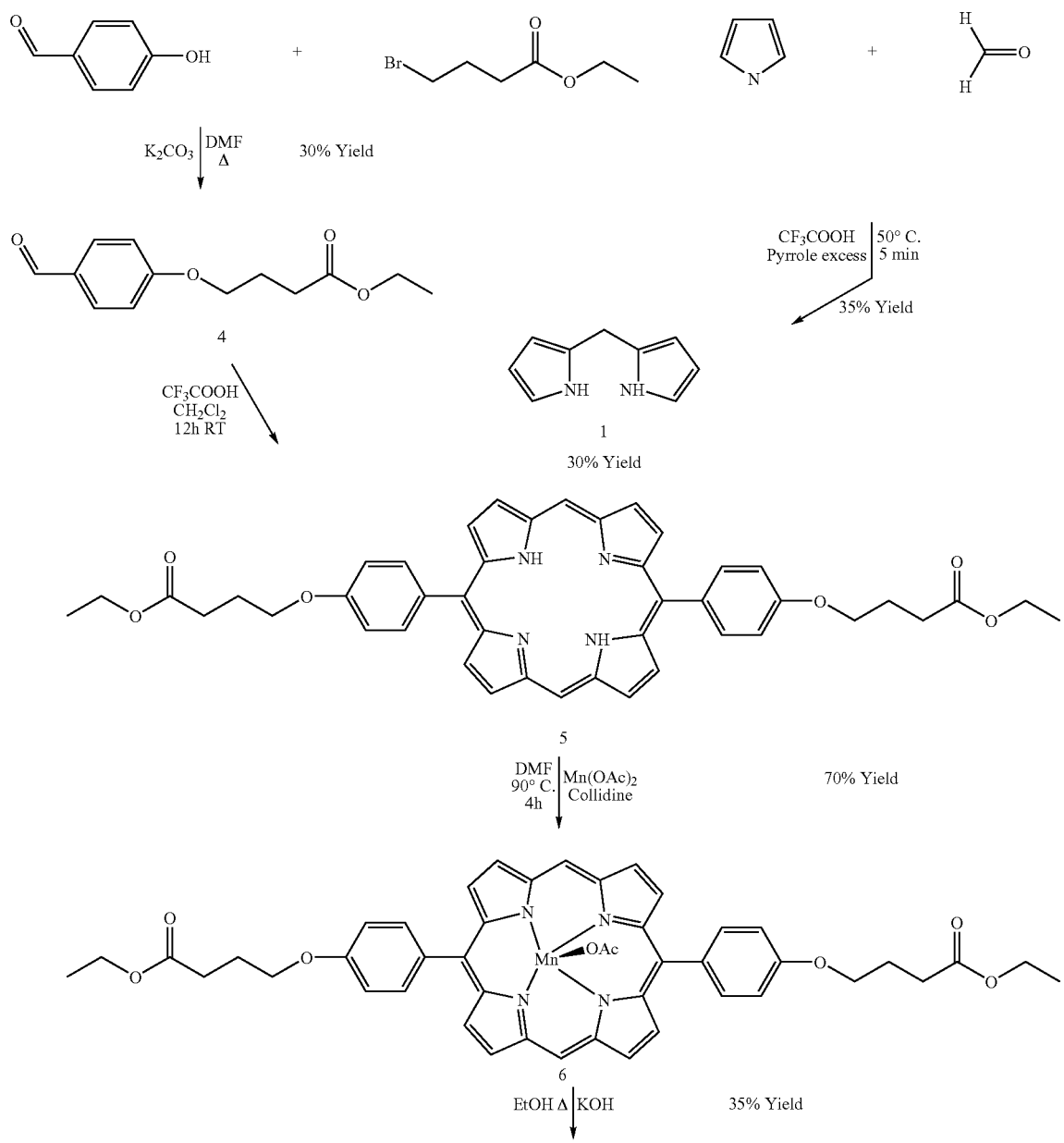

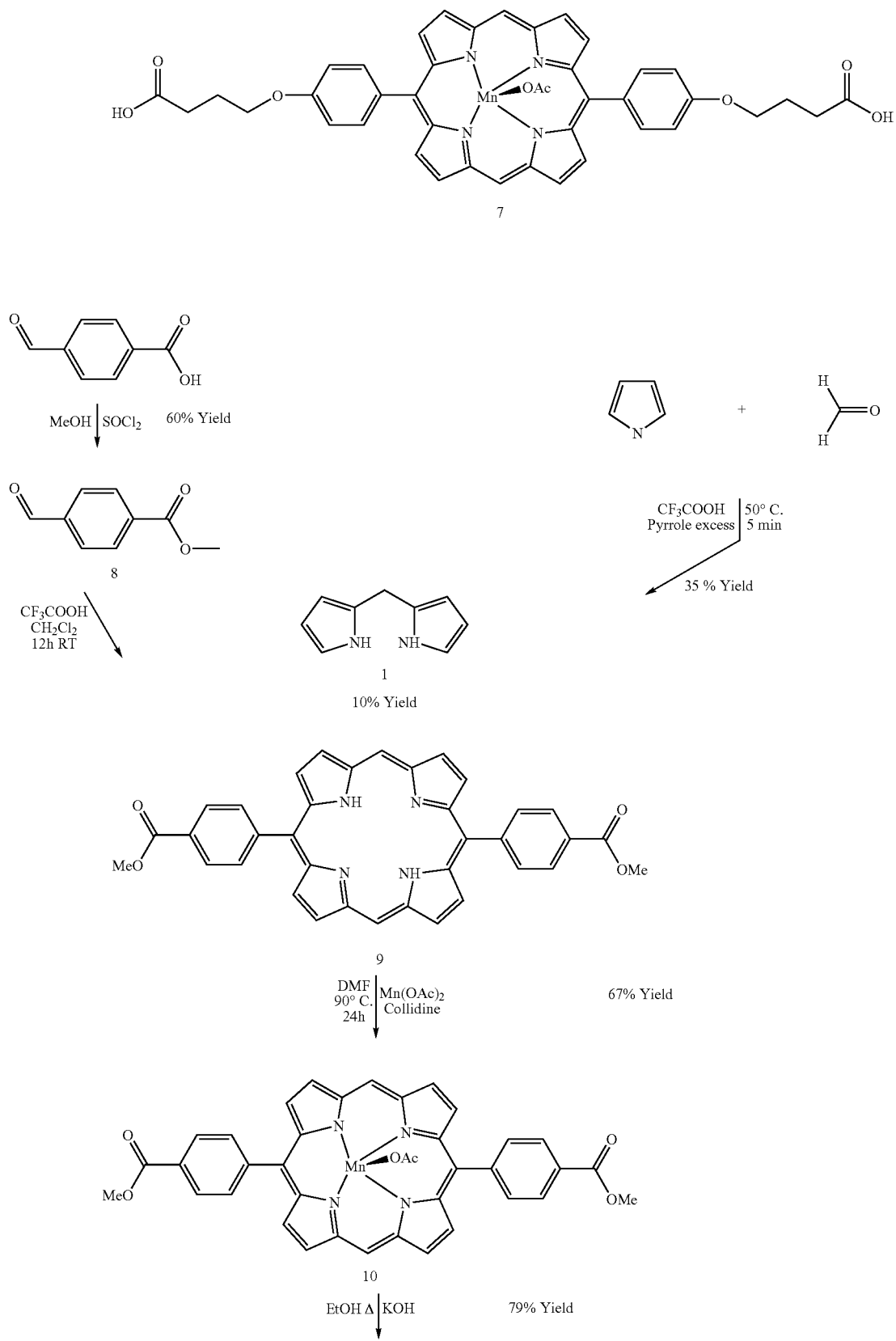

-continued
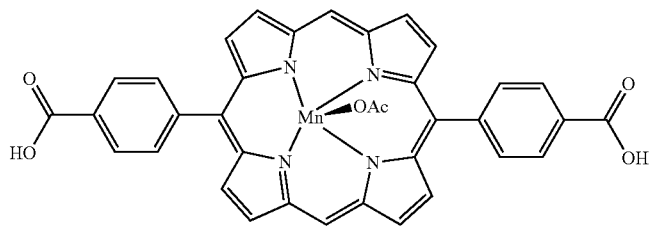
11
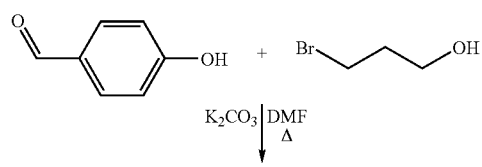
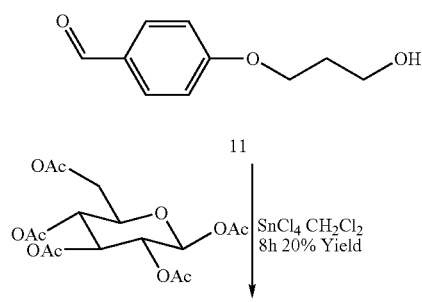
12
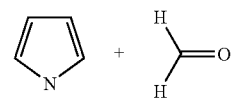
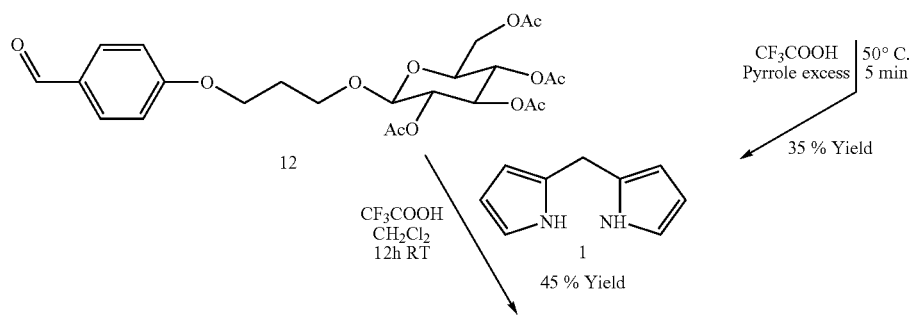
13
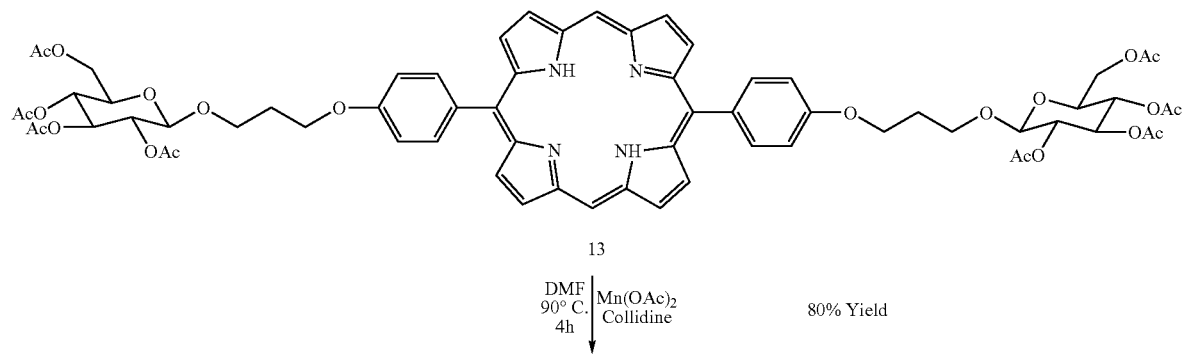

-continued
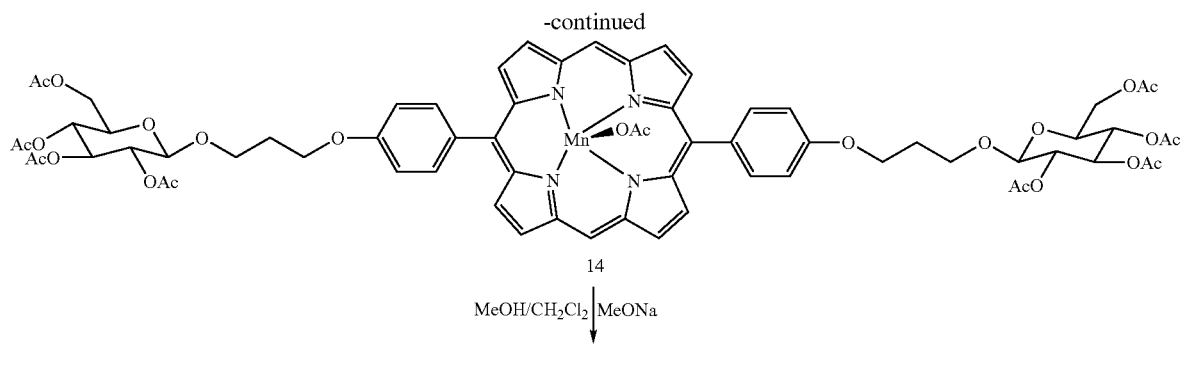
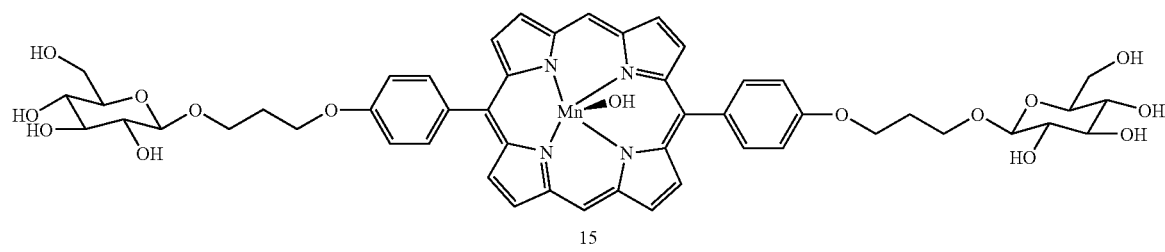
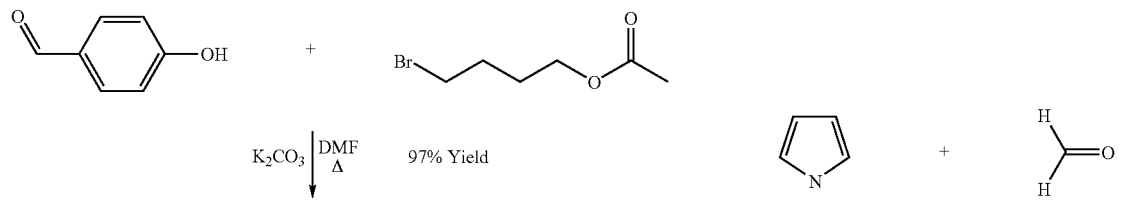
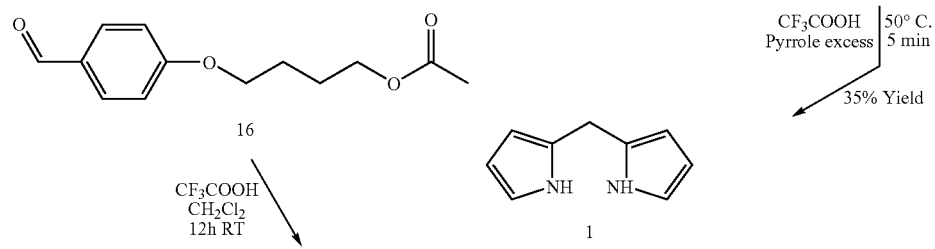
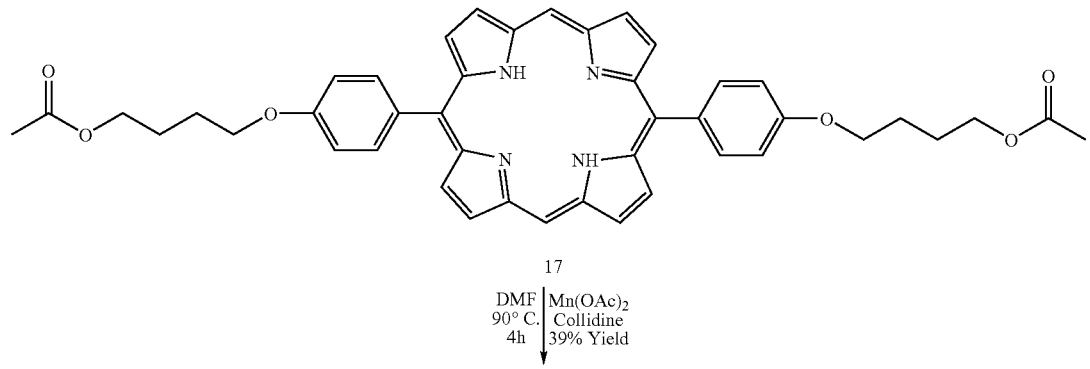

-continued
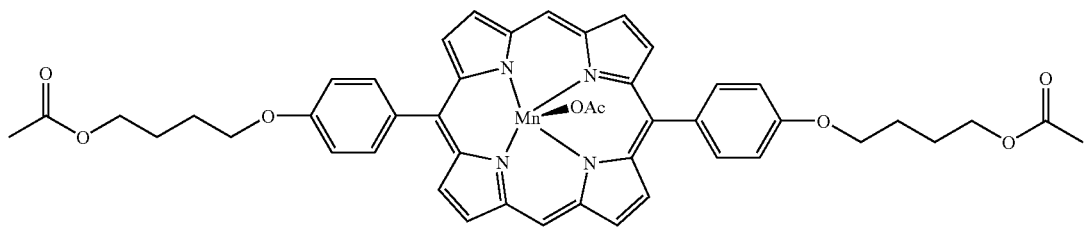
18
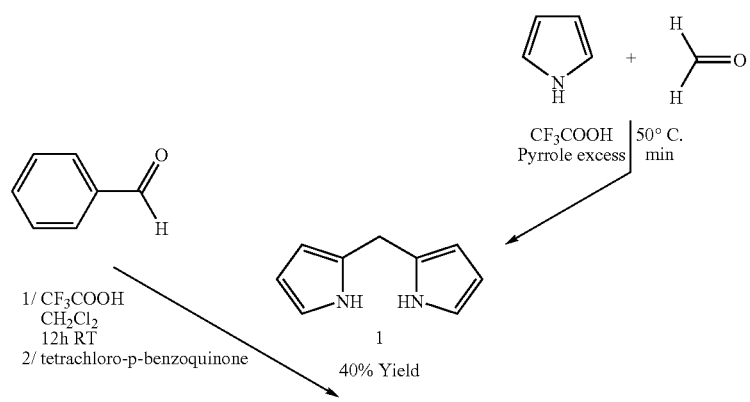
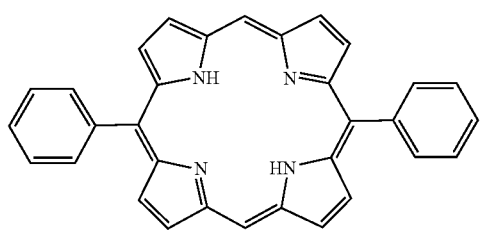
19
DMF | Mn(OAc)$_2$
Δ | Collidine
4h | 10% Yield
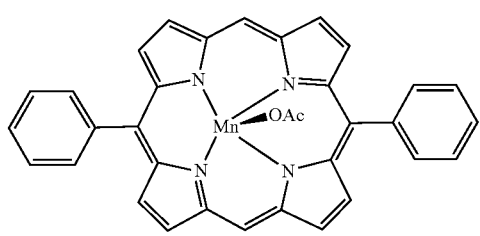
20

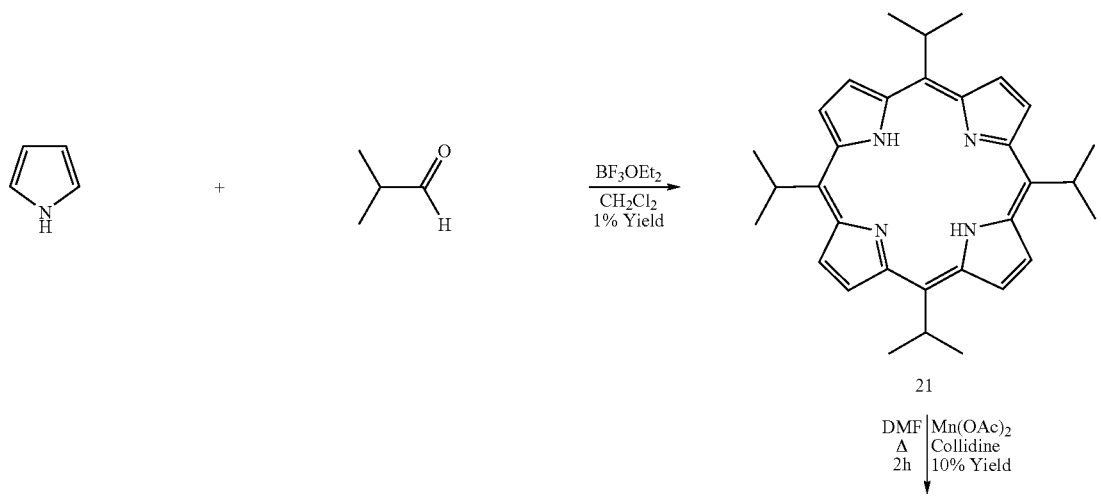
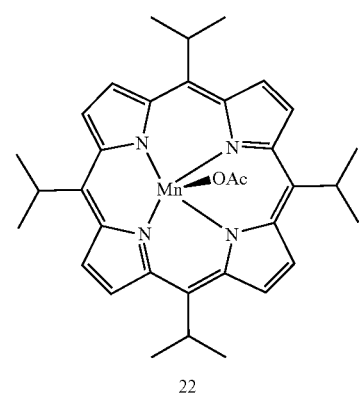
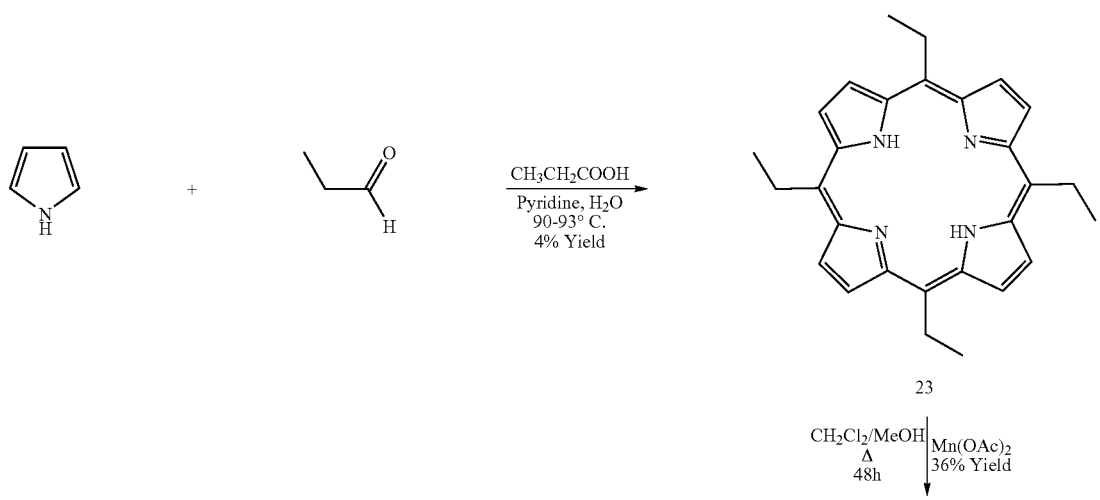

-continued
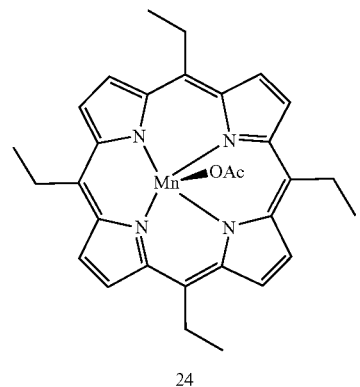
24
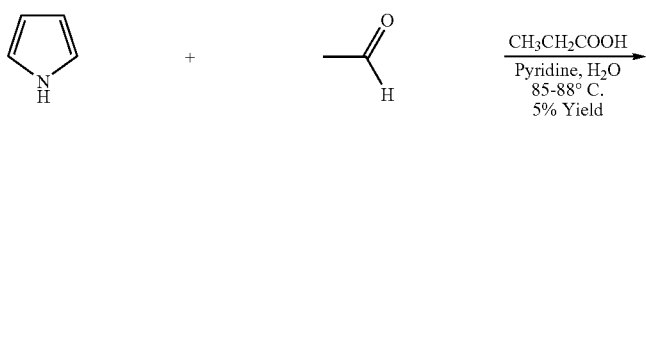
25
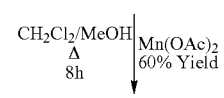
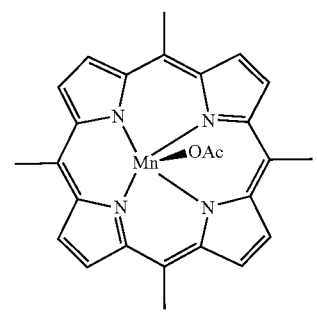
26
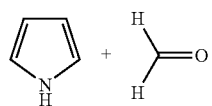

-continued

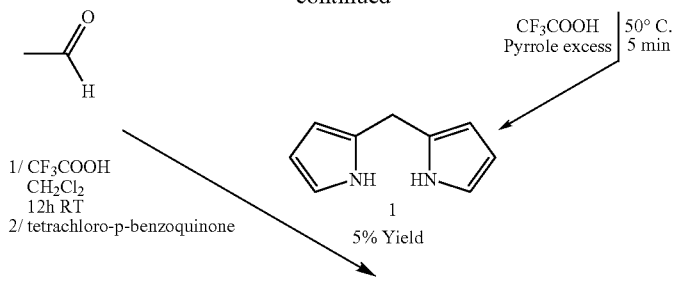

1
5% Yield

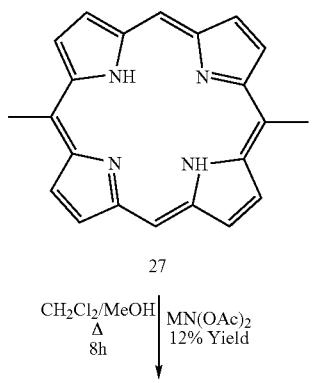

27

CH$_2$Cl$_2$/MeOH  MN(OAc)$_2$
Δ          12% Yield
8h

28

Animal Bioavailability of {[{(Porphine-5,15-diyl)bis[cyclopropyl-diyl]}](2-)-N$^{21}$,N$^{22}$, N$^{23}$, N$^{24}$}manganese(III)acetate (Compound 3)

| Time | Plasma (ng/ml) | Brain (ng/g) | Kidney (ng/g) | Liver (ng/g) | Lung (ng/g) |
|---|---|---|---|---|---|
| IV 82 min | 458 | 25 | 6,450 | 2,033 | 444 |
|  | 223 | 75 | 9,283 | 3,176 | 722 |
|  | 341 | 50 | 7,867 | 2,605 | 583 |
| Oral 70 min | 50 | 88 | 3,433 | 922 | 6,357 |
|  | 41 | 24 | 1,773 | 108 | 504 |
|  | 46 | 56 | 2,603 | 515 |  |
|  | (13%) | (112%) | (33%) | (20%) |  |
| IV 238 min | 161 | 89 | 8,458 | 2,303 | 667 |
|  | 50 | 91 | 4,925 | 1,482 | 362 |
|  | 106 | 90 | 6,692 | 1,893 | 515 |
| Oral 234 min | 3 | 8 | 452 | 132 | 48 |
|  | 1 | 9 | 370 | 80 | 85 |
|  | 2 | 9 | 411 | 106 | 67 |
|  | (2%) | (10%) | (6%) | (6%) | (13%) |

{[{(Porphine-5,15-diyl)bis[cyclopropyl-diyl]}](2-)-N$^{21}$,N$^{22}$,N$^{23}$,N$^{24}$}manganese(III) acetate (Compound 3) Oral Route Bioavailability Materials and Methods Animals Twenty 8-week-old Balb/c male mice (Charles River, US) were used in all experiments. Mice were kept at a temperature of 22±3° C. and provided with a standard diet and water.

For i.v. experiment mice received standard food before and during the experiment. For oral route, mice received no food 3 h before the start of the experiment and no food after.

Experimental Procedures 1. i.v. Experiment:

0.1 mL of a solution of Compound 3, 3 mg/mL in mannitol 5% (previously sterilized by filtration onto Acrodisc® syringe filter 0.2 μm HT Tuffryn® membrane) was injected in the tail vein. Two animals were killed 0.5 h after injection, two animals were killed 1 h after injection, two animals were killed 2 h after injection and two animals were killed 4 h after injection.

At the time of sacrifice, mice were bled by heart puncture. Then organs were removed for biochemical studies (brain, kidney, liver and lung).

2. Oral Route Experiment

Animals received by gavage a 0.1 mL of a solution of Compound 3 3 mg/mL in mannitol 5% (previously sterilized by filtration onto Acrodisc® syringe filter 0.2 mm HT Tuffryn® membrane). Two animals were killed 0.5 h after gavage, two animals were killed 1 h after gavage, two animals were killed 2 h after gavage and two animals were killed 4 h after gavage.

At the time of sacrifice, mice were bled by heart puncture. Then organs were removed for biochemical studies (brain, kidney, liver and lung).

Biochemical Study

Blood:

Red blood cells and plasma were separated by addition of heparine (15 μL) and centrifugation (2000 rpm, 5 min). Then 1.5 mL of HPLC mobil phase (Ammonium acetate 3 mM, acetonitrile, methanol, formic acid; 1/1/1/0.07 (v/v) at pH=3) were added to 40 μL of plasma and the mixture was centrifugated (2000 rpm, 5 min). The liquid layer (50 μL) was then analysed by LC/MS (MRM procedure, Column PARTISIL 5 ODS-3 RAC II, Cat. no. 4222-225).

Organs:

Organs were washed with 5 ml of distilled water and dried with blotting paper. Volumes of organs were measured by addition of the organ into one half full of water graduated test tube. Organs were dried a second time with blotting paper and then weighed. A volume of mobil phase (in mL) corresponding to 6 times of the organ weigh (in g) was added to the organ. The mixture was crushed mechanically (with JANKE & KUNKEL, IKA Labortechnik ULTRA-TURRAX T25; 24000 rpm, 1 min), sonicated 30 min and centrifugated 20 min (2000 rpm). To this mixture, 1 mL of the liquid layer was removed and filtrated with Acrodisc CRPTFE® syringe Filter in order to obtain a clear solution suitable for LC/MS analysis.

All references cited herein are incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A complex comprising manganese (III) acetate and a compound represented by Structural Formula I Structural Formula I wherein $R_1$ and $R_2$ are each independently lower alkyl, cycloalkyl, benzoic acid, methylbenzoate, phenyl, ethylbutanoate phenyl ether, butyl ethanoate phenyl ether, butanoic acid phenyl ether, or tetra-O-acetyl-β-D-glucosyloxypropyl phenyl ether.

2. The complex of claim 1 consisting of {[{(Porphine-5,15-diyl)bis[cyclopropyl-diyl]}](2-)-$N^{21},N^{22},N^{23},N^{24}$}manganese (III) acetate.

3. A pharmaceutical formulation comprising one or more pharmaceutically acceptable carriers, diluents or excipients and an amount of at least one complex of claim 1 sufficient to reduce or prevent oxyradical-induced or reactive oxygen-induced damage to cells.

4. A pharmaceutical formulation of claim 3 wherein the complex consists of {[{(Porphine-5,15-diyl)bis[cyclopropyl-diyl]}](2-)-$N^{21},N^{22},N^{23}, N^{24}$}manganese (III) acetate.

5. The pharmaceutical formulation of claim 3 wherein the complex is formulated as an oral composition.

6. The complex of claim 1 selected from the group consisting of:

{[{(Porphine-5,15-diyl)bis[cyclopropyl-diyl]}](2-)-$N^{21}, N^{22},N^{23},N^{24}$}manganese(III) acetate, {[Diethyl-4,4'-{(Porphine-5,15-diyl)bis[benzene-1,4-diyl(oxy)]{bis(butanoato)](2-)-$N^{21}, N^{22},N^{23},N^{24}$}manganese (III) acetate, {[{(Porphine-5,15-diyl)bis[benzene-1,4-diyl(oxy)]}bis (butanoic acido)](2-)-$N^{21},N^{22}, N^{23},N^{24}$}manganese III acetate, {[{(Porphine-5,15-diyl)bis[methyl 4-benzoate-1,4-diyl]}])](2-)-$N^{21},N^{22},N^{23},N^{24}$}manganese (III) acetate, {{Porphine-5,15-diyl)bis[benzene-1,4-diyl(4-[3-(2,3,4,6-Tetra-O-acetyl-β-D -glucosyloxy)propyl-oxy)]}(2-)$N^{21}, N^{22},N^{23},N^{24}$}manganese (III) acetate, {{Porphine-5,15-diyl)bis[benzene-1,4-diyl(oxy)]butylactetate}(2-)$N^{21},N^{22},N^{23},N^{24}$}manganese (III) acetate, {[{Porphine-5,15-diyl)bis[benzyl-diyl]}])](2-) $N^{21},N^{22}, N^{23},N^{24}$}manganese (III) acetate, and {[{Porphine-5,15-diyl-bis[methyl-diyl]}](2-) $N^{21},N^{22}, N^{23},N^{24}$}manganese (III) acetate.

7. A pharmaceutical formulation comprising one or more pharmaceutically acceptable carriers, diluents or excipients and an amount of at least one complex according to claim 6 sufficient to reduce or prevent oxyradical-induced or reactive oxygen-induced damage to cells.

* * * * *

UNITED STATES PATENT AND TRADEMARK OFFICE
CERTIFICATE OF CORRECTION

PATENT NO.       : 7,649,091 B2                                                                 Page 1 of 1
APPLICATION NO.  : 10/559221
DATED            : January 19, 2010
INVENTOR(S)      : Meunier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this

Twenty-third Day of November, 2010

David J. Kappos
*Director of the United States Patent and Trademark Office*